(12) United States Patent
DeRocher et al.

(10) Patent No.: US 8,653,325 B2
(45) Date of Patent: Feb. 18, 2014

(54) INCREASED SEED SIZE AND SEED NUMBER THROUGH TRANSGENIC OVER EXPRESSION OF REVOLUTA PROTEIN DURING EARLY EMBRYO DEVELOPMENT

(75) Inventors: Jay DeRocher, Bothell, WA (US); Thu Nguyen, Brier, WA (US)

(73) Assignee: Targeted Growth, Inc., Seattle, WA (US)

( * ) Notice: Subject to any disclaimer, the term of this patent is extended or adjusted under 35 U.S.C. 154(b) by 767 days.

(21) Appl. No.: 11/611,832

(22) Filed: Dec. 15, 2006

(65) Prior Publication Data
US 2008/0263727 A1 Oct. 23, 2008

Related U.S. Application Data

(60) Provisional application No. 60/750,991, filed on Dec. 15, 2005.

(51) Int. Cl.
*A01H 1/00* (2006.01)

(52) U.S. Cl.
USPC .............................. 800/278; 800/290; 800/287

(58) Field of Classification Search
None
See application file for complete search history.

(56) References Cited

U.S. PATENT DOCUMENTS

| | | | |
|---|---|---|---|
| 6,437,219 | B1 | 8/2002 | Grimes et al. |
| 7,056,739 | B1 * | 6/2006 | Slade et al. ................... 435/419 |
| 2004/0187176 | A1 | 9/2004 | Boyes et al. |
| 2004/0221332 | A1 | 11/2004 | Lorbiecke et al. |

FOREIGN PATENT DOCUMENTS

| | | | |
|---|---|---|---|
| WO | WO 01/33944 | * | 5/2001 |
| WO | WO 0133944 A1 | | 5/2001 |
| WO | WO 2005075655 A1 | | 8/2005 |

OTHER PUBLICATIONS

Kano-Murakami et al (1993, FEBS 334:365-368).*
Barrero et al., "Over-expression of *Arabidopsis* CAP causes decreased cell expansion leading to organ size reduction in transgenic tobacco plants," *Annals of Botany* 91:599-603 (2003).
Bonaventure et al., "Disruption of the *FATB* gene in *Arabidopsis* demonstrates an essential role of saturated fatty acids in plant growth," *Plant Cell* 15:1020-1033 (2003).
Broun et al., "A bifunctional oleate 12-hydroxylase: desaturase from *Lesquerella fendleri*," *Plant J.* 13:201-210 (1998).
Bustos et al., "Regulation of β-glucuronidase expression in transgenic tobacco plants by an A/T-rich, *cis*acting sequence found upstream of a French bean β-phasseolin gene," *Plant Cell* 1:839-854 (1989).
Chen et al., "A seven-transmembrane RGS protein that modulates plant cell proliferation," *Science* 301:1728-1731 (2003).

Colombo et al., "Downregulation of ovule-specific MADS box genes from petunia results in maternally controlled defects in seed development," *Plant Cell* 9:703-715 (1997).
Cushing et al., "*Arabidopsis emb* 175 and other *ppr* knockout mutants reveal essential roles for pentatricopeptide repeat (PPR) proteins in plant embryogenesis," *Planta* 221:424-436 (2005).
Debeaujon et al., "The *TRANSPARENT TESTA12* gene of *Abrabidopsis* encodes a multidrug secondary transporter-like protein required for flavonoid sequestration in vacuoles of the seed coat endothelium," *Plant Cell* 13:853-871 (2001).
del Pozo et al., "The balance between cell division and endoreplication depends on E2FC-DPB, transcription factors regulated by the ubiquitin-SCF$^{SKP2A}$ pathway in *Arabidopsis*," *Plant Cell* 18:2224-2235 (2006).
Devic et al., "The *BANYULS* gene encodes a DFR-like protein and is a marker of early seed coat development," *Plant J.* 19:387-398 (1999).
Disch et al., "The E3 ubiquitin ligase Big Brother controls *Arabidopsis* organ size in a dosage-dependent manner," *Curr. Biol.* 16:272-279 (2006).
Emery et al., "Radial patterning of *Arabidopsis* shoots by class III HD-ZIP and Kanadi genes," *Curr. Biol.* 13:1768-1774 (2003).
Foreman et al., "Reactive oxygen species produced by NADPH oxidase regulate plant cell growth," *Nature* 422:442-446 (2003).
Green et al., "Binding site requirements for pea nuclear protein factor GT-1 correlate with sequences required for light-dependent transcriptional activation of the *rbcS-3A* gene," *EMBO J.* 7:4035-4044 (1988).
Guerche et al., "Differential Expression of the *Arabidopsis* 2S Albumin Genes and the Effect of Increasing Gene Family Size," *Plant Cell* 2:469-478 (1990).
Haberer et al., "The *Arabidopsis* gene Pepino/*Pasticcino2*is required for proliferation control of meristematic and non-meristematic cells and encodes a putative anti-phosphatase," *Dev. Genes Evol.* 212:542-550 (2002).
Haslekas et al., "The expression of a peroxiredoxin antioxidant gene, *AtPer1* , in *Arabidopsis thaliana* is seed-specific and related to dormancy," *Plant Mol Biol.* 36:833-845 (1998).
Haslekas et al., "ABI3 mediates expression of the peroxiredoxin antioxidant *AtPER1* gene and induction by oxidative stress," *Plant Mol. Biol.* 53:313-326 (2003).
Hemsley et al., "The Tip Growth Defective1 S-acyl transferase regulates plant cell growth in *Arabidopsis*," *Plant Cell* 17:2554-2563 (2005).
Heuer, "The maize MADS box gene *ZmMADS3* affects node number and spikelet development and is co-expressed with *ZmMADS1* during flower development, in egg cells, and early embryogenesis," *Plant Phys.* 127:33-45 (2001).
Hirner et al., "Developmental control of H+/amino acid permease gene expression during seed development of *Arabidopsis*," *Plant J.* 14:535-544 (1998).

(Continued)

*Primary Examiner* — Stuart F Baum
(74) *Attorney, Agent, or Firm* — Cooley LLP

(57) ABSTRACT

The present invention provides methods and compositions for increasing the seed size and/or seed number in plants. In particular, the methods and compositions provide for the over expression of a plant growth and/or development related or associated gene during embryo development. Transgenic plants transformed with genetic constructs having the plant growth and/or development associated gene under the control of an early phase-specific embryo promoter provides mature plants in the field that produce larger and/or more seeds. Methods for selection growth and development associated genes that provide transgenic plants with a higher yield phenotype are also provided.

24 Claims, 2 Drawing Sheets

(56) References Cited

OTHER PUBLICATIONS

Hu et al., "The *Arabidopsis ARGOS-LIKE* gene regulates cell expansion during organ growth,"*Plant J.* 47:1-9 (2006).
Inagaki et al., "*Arabidopsis* Tebichi, with helicase and DNA polymerase domains, is required for regulated cell division and differentiation in meristems," *Plant Cell* 18:879-892 (2006).
Jang et al., "Structure and expression of the rice class-I type histone deacetylase genes *OsHDAC1-3: OsHDAC1* overexpression in transgenic plants leads to increased growth rate and altered architecture," *Plant J.* 33:531-541 (2003).
Jordano et al., "A sunflower helianthinin gene upstream sequence ensemble contains an enhancer and sites of nuclear protein interaction," *Plant Cell* 1:855-866 (1989).
Keddie et al., "A seed-specific *Brassica napus* oleosin promoter interacts with a G-box-specific protein and may be bi-directional," *Plant Mol. Biol.* 24:327-340 (1994).
Kohler et al., "The *Polycomb*-group protein MEDEA regulates seed development by controlling expression of the MADS-box gene *PHERES1*," *Genes Develop.* 17:1540-1553 (2003).
Kohorn et al., "An *Arabidopsis* cell wall-associated kinase required for invertase activity and cell growth," *Plant J.* 46:307-316 (2006).
Kroj et al., "Regulation of storage protein gene expression in *Arabidopsis*," *Development* 130:6065-6073 (2003).
Kwong et al., "Leafy Cotyledon1-Like defines a class of regulators essential for embryo development," *Plant Cell* 15:5-18 (2003).
Lally et al., "Antisense expression of a cell wall-associated protein kinase, WAK4, inhibits cell elongation and alters morphology," *Plant Cell* 13:1317-1331 (2001).
Lehti-Shiu et al., "Expression of MADS-box genes during the embryonic phase in *Arabidopsis*," *Plant Mol. Biol.* 58:89-107 (2005).
Lin and Zimmerman, "Expression of a globulin-like protein gene, *Gea8*, in somatic and zygotic embryos," *J. Exp. Botany* 50:1139-1147 (1999).
Lotan et al., "*Arabidopsis* Leafy Cotyledon1 is sufficient to induce embryo development in vegetative cells," *Cell* 93:1195-1205 (1998).
McConnell and Barton, "Leaf polarity and meristem formation in *Arabidopsis*," *Development* 125:2935-2942 (1998).
McConnell et al., "Role of *PHABULOSA* and *PHAVOLUTA* in determining radial patterning in shoots," *Nature* 411:709-713 (2001).
Meier et al., "Elicitor-inducible and constitutive in vivo DNA footprints indicate novel *cis*-acting elements in the promoter of a parsley gene encoding pathogenesis-related protein 1," *Plant Cell* 3:309-316 (1991).
Nesi et al., "The *TT8* gene encodes a basic helix-loop-helix domain protein required for expression of *DFR* and *BAN* genes in *Arabidopsis* siliques," *Plant Cell* 12:1863-1878 (2000).
Nesi et al., "The *Transparent Testa16* locus encodes the *Arabidopsis* Bsister MADS domain protein and is required for proper development and pigmentation of the seed coat," *Plant Cell* 14:2463-2479 (2002).
Ng et al., "The 5' UTR negatively regulates quantitative and spatial expression from the *ABI3* promoter," *Plant Mol. Biol.* 54:25-38 (2004).
Ohto et al., "Control of seed mass by *APETALA2*," *Proc. Natl. Acad. Sci. USA* 102:3123-3128 (2005).
Otsuga et al.,"*REVOLUTA* regulates meristem initiation at lateral positions," *Plant J.* 25:223-236 (2001).
Parcy et al., "Regulation of gene expression programs during *Arabidopsis* seed development: roles of the *ABI3* locus and of endogenous abscisic acid," *Plant Cell* 6:1567-1582 (1994).
Pinyopich et al., "Assessing the redundancy of MADS-box genes during carpel and ovule development," *Nature* 424:85-88 (2003).
Plant et al., "Regulation of an *Arabidopsis* oleosin gene promoter in transgenic *Brassica napus*," *Plant Mol. Biol.* 25:193-205 (1994).
Postma-Haarsma et al., "Characterization of the KNOX class homeobox genes *Oskn2* and *Oskn3* identified in a collection of cDNA libraries covering the early stages of rice embryogenesis," *Plant Mol. Biol.* 39:257-271 (1999).
Rossak et al., "Expression of the *FAE1* gene and *FAE1* promoter activity in developing seeds of *Arabidopsis thaliana*," *Plant Mol. Biol.* 46:717-725 (2001).
Ruan et al., "Suppression of sucrose synthase gene expression represses cotton fiber cell initiation, elongation, and seed development," *Plant Cell* 15:952-964 (2003).
Ryan et al., "*TIP1* is required for both tip growth and non-tip growth in *Arabidopsis*," *New Phytol.* 138:49-58 (1998).
Sagasser et al., "*A. thaliana* Transparent Testa 1 is involved in seed coat development and defines the WIP subfamily of plant zinc finger proteins," *Genes Dev.* 16:138-149 (2002).
Simmonds and Donaldson, "Genotype screening for proliferative embryogenesis and biolistic transformation of short-season soybean genotypes," *Plant Cell Reports* 19:485-490 (2000).
Talbert et al., "The *REVOLUTA* gene is necessary for apical meristem development and for limiting cell divisions in the leaves and stems of *Arabidopsis thaliana*," *Development* 121:2723-2735 (1995).
Tsuchiya et al., "The *FUS3* transcription factor functions through the epidermal regulator TTG1 during embryogenesis in *Arabidopsis*," *Plant J.* 37:73-81 (2004).
Vilhar et al., "Cytometrical evidence that the loss of seed weight in the *miniature1* seed mutant of maize is associated with reduced mitotic activity in the developing endosperm,"*Plant Physiol.* 129: 23-30 (2002).
Wagner and Kohorn, "Wall-associated kinases are expressed throughout plant development and are required for cell expansion," *Plant Cell* 13:303-318 (2001).
Walker et al., "The *Transparent Testa Glabra1* locus, which regulates trichome differentiation and anthocyanin biosynthesis in *Arabidopsis*, encodes a WD40 repeat protein," *Plant Cell* 11:1337-1349 (1999).
Wang et al., "Autoregulation and homodimerization are involved in the activation of the plant steroid receptor BRI1," *Dev. Cell* 8:855-865 (2005).
Wang and Chory, "Brassinosteroids regulate dissociation of BKI1, a negative regulator of BRI1 signaling, from the plasma membrane," *Science* 313:1118-1122 (2006).
Zhang et al., "DNA sequences that activate isocitrate lyase gene expression during late embryogenesis and during postgerminative growth," *Plant Physiol.* 110:1069-1079 (1996).
Zou and Taylor, "Cloning and molecular characterization of an *Arabidopsis thaliana* RING zinc finger gene expressed preferentially during seed development," *Gene* 196:291-295 (1997).
Examination Report based on Australian Patent Application No. 2006332574, mailed on Jul. 5, 2011.
Sakulsingharoj et al., "Engineering starch biosynthesis for increasing rice seed weight: the role of the cytoplasmic ADP-glucose pyrophosphorylase", *Plant Science*, 167(6):1323-1333, Dec. 1, 2004.
European Search Report and Supplemental Search Report based on corresponding European Application No. EP06849023.4, mailed on Aug. 6, 2009.
Examination Report based on Canadian Patent Application No. 2,633,988, mailed on Sep. 10, 2012.
Search Report based on European Patent Application No. 11190538. 6, mailed on May 30, 2012.
English translation of Examination Report based on Chinese Patent Application No. 200680052853.3, mailed on Dec. 26, 2012.
Rolletschek et al. "Ectopic expression of an amino acid transporter (VfAAP1) in seeds of *Vicia* narbonensis and pea increases storage proteins" Plant Physiology, Apr. 1, 2005, 137(4):1236-1249.
English translation of Examination Report based on Chinese Patent Application No. 200680052753.3, mailed on Feb. 16, 2011.
Examination Report based on European Patent Application No. 06849023.4, mailed on Jul. 19, 2010.
English translation of Examination Report based on Israeli Patent Application No. 192077, mailed on Jul. 11, 2010.
Examination Report based on New Zealand Patent Application No. 569054, mailed on Apr. 16, 2010.
English translation of Examination Report based on Russian Patent Application No. 2008123381, mailed on Sep. 23, 2010.

\* cited by examiner

| | | |
|---|---|---|
| Athb-9 | 113 | NLVYENGFMKHRIHTASGTTTDNSCESVVVSGQ QRQQQNPTHQ HPQRDVNNPANLLSIAE |
| Athb-14 | 117 | NLVYENGHMKHQLHTASGTTTDNSCESVVVSGQ HQQQNPNPQ HQQRDANNPAGLLSIAE |
| REV | 117 | QLVCENGYMKQQLTTVVN---DPSCESVVTTPQ ---------- HSLRDANSPAGLLSIAE |
| BnLfREV | 118 | HLVSENGYMQQQLTLTLGTDASCDSVDPTPPL ---------- HPLRDANSPAGLMAIAE |
| OsREV1 | 119 | QLVHENAHMRQQLQNTPLAN-DTSCESNVTTPQ ---------- NPLRDASNPSGLLSIAE |
| ZmRLD1 | 119 | QLVHENAHMKQQLQNTSLAN-DTSCESNVTTPQ ---------- NPLRDASNPSGLLAIAE |
| OsREV2 | 121 | QLVHENAYMKQQLQNPSLGN-DTSCESNVTTPP ---------- NPLRDASNPSGLLTIAE |
| Athb-15 | 109 | QLVHENSYFRQHTPNP-SLPAKDTSCESVVTSG ----QHQLAS QNPQRDASPAGLLSIAE |
| Athb-8 | 107 | HLVYENSYFRQHPQNQGNLATTDTSCESVVTSG ----QHHLTP QHQPRDASPAGLLSIAD |

FIG. 2

INCREASED SEED SIZE AND SEED NUMBER THROUGH TRANSGENIC OVER EXPRESSION OF REVOLUTA PROTEIN DURING EARLY EMBRYO DEVELOPMENT

CROSS-REFERENCES TO RELATED APPLICATIONS

This application claims priority to U.S. Patent Application No. 60/750,991, filed on Dec. 15, 2005, incorporated by reference herein in its entirety for all purposes.

DESCRIPTION OF THE TEXT FILE SUBMITTED ELECTRONICALLY

The contents of the text file submitted electronically herewith are incorporated herein by reference in their entireties: A computer readable format copy of the Sequence Listing (filename: TARG-007-01US.txt, date recorded: Jun. 4, 2010, file size 16 kilobytes).

BACKGROUND OF THE INVENTION

The most important trait as a target for crop improvement is yield. Efforts to improve crop yields by developing new plant varieties can be divided into two approaches. One is to reduce crop yield losses by breeding or engineering crop varieties with increased resistance to abiotic stress conditions such as drought, cold, or salt or to biotic stress conditions resulting from pests or disease-causing pathogens. While this approach has value, it does not provide fundamentally improved crop yield in the absence of stress conditions.

The second approach is to breed or engineer new crop varieties in which the basic yield capacity is increased. Classical breeding programs have initially produced substantial gains in improved yield in a variety of crops. A commonly experienced pattern though has been substantial gains in yield initially followed by incremental further improvements that become smaller and more difficult to obtain.

More recently developed approaches based on molecular biology technologies have in principle offered the potential to achieve substantial improvement in crop yield by altering the timing, location, or level of expression of plant genes that play a role in plant growth and/or development. Substantial progress has been made over the past twenty years in identifying plant genes that have a role in plant growth and/or development. Because of the complexity of plant growth regulation and how it relates in the end to yield traits, it is still not obvious which, if any, of these genes would be a clear candidate to improve crop yield.

Much of the work that has been done to identify plant genes with a growth and/or development function has been done in the model plant system *Arabidopsis thaliana*. One such gene, called REVOLUTA (REV), was originally identified as a loss-of-function mutation in *Arabidopsis* called rev1 (Talbert et al., *Development* 121:2723-2735, 1995). This mutation had pleiotropic effects on plant growth and morphology. One phenotype of the rev1 mutation that was of interest was significantly larger seeds. This phenotype was potentially desirable agriculturally but, unfortunately, it was accompanied by undesirable traits such as reduced numbers of flowers and seeds, infertility, and altered leaf morphology. The rev1 mutant exhibits larger leaves, stems, and flowers in addition to larger seeds.

The REV gene was identified by a map based cloning approach (described in WO 01/33944, incorporated herein by reference in its entirety) and it proved to be a transcription factor that belonged to the homeodomain-leucine zipper (HD-ZIP) family of transcription factors. In plants, HD-Zip genes are involved in many developmental pathways, including vascular tissue development, trichome and root hair development, and light-regulated responses. Since rev1 was likely to be a loss of function mutation, efforts were made to knock out REV function in transgenic *Arabidopsis* by expressing inverted repeat REV (REV-IR) constructs or via co-suppression triggered by strong over expression of the REV gene (WO 01/33944). REV-IR constructs gave a weak rev1 phenotype. The rev1 phenotype including larger, heavier seeds was also observed in REV over expression lines where strong constitutive expression of the REV transgene throughout the plant was driven by the constitutive 35S promoter. Interestingly, this effect correlated with increased REV mRNA levels indicating that it was not due to co-suppression of the endogenous REV gene. The fact that REV over expression and not suppression gave increased seed size was an important finding because it was unanticipated based on the prior work with the rev1 mutant.

Strong constitutive expression of the REV transgene throughout the plant mimicked the large seed phenotype of the rev1 mutant, but it also replicated undesirable phenotypes seen with the rev1 mutant. While the ability to obtain the larger seed size phenotype by the technically straight forward approach of constitutive over expression of a REV transgene showed promise, the undesirable phenotypes meant that this approach would not be viable for commercial agricultural applications.

The agriculturally relevant part of the plant for many crop species is the seed. If the large seed trait could be obtained without the detrimental side effects of general constitutive REV over expression, it would be of potentially great agricultural value. One conceivable approach to overcome this problem was to limit REV over expression specifically to the seed. While many seed-specific promoters are already known and characterized that could potentially be used to drive REV transgene expression, there was no evidence to suggest that, in principle, REV over expression limited to the seed would actually result in increased seed size. The natural function of a plant's endogenous REV gene in the seed is known to be in meristem initiation and adaxial cell fate determination (Otsuga et al., *Plant J.* 25:223-236, 2001; McConnell and Barton, *Development* 125:2935-2942 (1998); McConnell et al., *Nature* 411:709-713, 2001; Emery et al., *Curr. Biol.* 13:1768-1774, 2003) and not in cell growth or division. Further, it is not known whether the large seed size phenotype in the 35S/REV over expression plants is due to over expression of REV in the seed or in the developing embryo or is instead due to effects on the overall growth and development of the plant caused by REV over expression throughout the plant's tissues.

In addition to the lack of any known biological function for REV in the seed that would have an effect on seed size determination, there is no information to indicate in what part of the seed or during what stage during seed development it might be best to attempt to over express a REV transgene to achieve an increase in seed size.

The present invention provides for the embryo-specific over expression of a growth and/or development related gene during an early stage of embryo development that results in an increase in seed size when compared to a wild-type plant that does not over express the gene. In a particular embodiment the REV gene was overexpressed using an early embryo-specific promoter. The increased seed size trait was achieved without the detrimental side effects seen with constitutive over expression of REV throughout the plant. In addition, embryo-specific over expression of REV gave the unpredicted result of an increase in total seed number per plant when compared to a wild-type plant. The increase in total seed number resulted from an increase in seed number per pod, an increase in the number of racemes per plant, an increase in the number of pods per raceme, a decrease in the rate of seed abortion, or a combination of these effects. Together, the increased seed size and increased seed number resulting from over expression of REV in the developing embryo lead to substantial increases in total yield when compared to a wild-type plant and demonstrates that a gene associated with plant growth and/or development can be overexpressed in association with an early embryo-specific promoter to increase plant yield.

BRIEF SUMMARY OF THE INVENTION

The present invention provides methods and compositions for increasing the seed size and/or seed number in transgenic plants. In particular, the present invention relates to the use of early phase-specific embryo promoters operatively associated with a gene associated with plant growth and/or development to provide for the over expression of the gene and/or a protein encoded by the gene in a developing seed of a transgenic plant. Over expression of the gene during this early stage of seed development in a transgenic plant provides for increased seed production and/or increased seed size in the transgenic plant when compared with the wild-type plant.

In a particular embodiment of the present invention the REV gene was operatively associated with an early phase-specific embryo promoter to provide for the over expression of REV protein in a developing seed of a transgenic plant. Over expression of REV during this early stage of seed development surprisingly resulted in increased seed size and increased seed production in the transgenic plant without the detrimental side effects that had been seen when REV was over expressed throughout the plant.

A method for increasing seed size in a plant comprising over expressing a gene associated with plant growth and/or development in a seed during early embryo development is also provided. In particular, the method comprises expressing the growth and/or development related gene in the seed under the control of an early phase-specific embryo promoter. The early phase-specific embryo promoter can be heterologous or homologous to the plant. In certain embodiments of the present invention the promoter is an early phase-specific promoter associated with an amino acid permease gene, such as AAP1, an oleate 12-hydroxylase:desaturase gene, a 2S2 albumin gene, a fatty acid elongase gene, such as FAE1, or a leafy cotyledon gene. Particular promoters useful in the present invention include the AAP1 promoter from *Arabidopsis thaliana*, an oleate 12-hydroxylase:desaturase gene promoter from *Lesquerella fendleri* (LFAH12), a 2S2 gene promoter or a leafy cotyledon gene LEC2 promoter from *Arabidopsis thaliana*.

In a particular embodiment of the present invention the REV gene was operatively associated with an early phase-specific embryo promoter. In this method, the REV gene was overexpressed in the early development of the seed and lead to an increase in seed size and seed number as compared with a wild-type plant.

The methods of the present invention can be used to increase the seed size and/or seed number in plants that are characterized as a monocot or a dicot. In particular, the methods can be used to increase the seed size and/or seed number in plants that are members of the Brassicacea, (Cruciferae), Gramineae, Malvaceae, or Leguminosae-Papilionoideae families. Particular plants of interest for use of the methods of the present invention include canola, corn, camelina, cotton, alfalfa, soybean, wheat, rice, or barley.

The present invention also provides genetic constructs comprising a nucleic acid sequence for a gene associated with plant growth and/or development is operatively linked to one or more control sequences wherein the one or more control sequences are capable of promoting expression of the gene during embryo development. In particular, the genetic construct of the invention comprise a control sequence including an early phase-specific embryo promoter. The early phase specific embryo promoters can include the promoter associated with an amino acid permease gene (AAP1), an oleate 12-hydroxylase:desaturase gene, an 2S2 albumin gene (2S2), a fatty acid elongase gene (FAE1), or a leafy cotyledon gene (LEC2). Typical genetic constructs of the present invention comprise the AAP1 promoter promoter from *Arabidopsis thaliana*, the oleate 12-hydroxylase:desaturase promoter from *Lesquerella fendleri* (LFAH12), the 2S2 gene promoter from *Arabidopsis thaliana*, the fatty acid elongase gene promoter from *Arabidopsis thaliana*, or the leafy cotyledon gene 2 promoter from *Arabidopsis thaliana*. Particular genetic constructs of the present invention comprise an early phase-specific embryo promoter operatively associated with a REV gene from *Arabidopsis*. The genetic construct can also include an operatively associated polyA sequence.

The present invention also provides methods for the production of a transgenic plant having increased seed size and/or seed number, the methods comprising: (a) introducing into a plant or into a plant cell, a genetic construct as set forth above and cultivating the plant or plant cell comprising the genetic construct under conditions promoting regeneration and mature plant growth. Typically, the methods produce a transgenic plant having increased seed size and/or seed number when compared to the corresponding wild-type plant. Transgenic plants comprising the genetic constructs can be monocotyledonous or a dicotyledonous plants, particularly where the monocotyledonous plant is a member of the Gramineae family. The plants from the Gramineae family of particular interest include rice, oat, corn, or wheat. Additionally, transgenic plants of the present invention are plants of the Brassicacea (Cruciferae), Malvaceae, or Leguminosae-Papilionoideae families. In particular wherein the transgenic plant is soybean, cotton, camelina, alfalfa, or canola.

The present invention also provides methods for selecting for a gene that increases plant yield when functionally associated with an early phase-specific embryo promoter; comprising construction an expression vector comprising a gene associated with plant growth and/or development functionally associated with a early phase-specific embryo promoter, transfecting a plant cell with the expression vector to form a transgenic plant; growing the transgenic plant and selecting those transgenic plants that have an increased yield. The genes that produce a transgenic plant with increased yield are selected for further development of transgenic plants. The genes that can be used in the present method include, for example, but are not limited to, the CAP (cyclase-associated protein) gene, the rice histone deacetylase 1 gene, E2Fc gene, BKI gene, the BRIJ gene, ARL (Argos-Like) gene, the bril (brassinosteroid hormone perception) gene, FATB gene, Pepino gene, RGS (regulator of G protein signaling) gene, the TIP1 gene, the BB (Big Brother) gene, the RHD2 gene, INCW2 gene, the MN1 gene, the WAK2 gene, the WAK4 gene, the AP2 gene, and the like.

BRIEF DESCRIPTION OF THE DRAWINGS

FIG. 2 depicts an alignment of amino acid sequences of a region of REVOLUTA and non-REVOLUTA HD-ZIPIII class transcription factors. This region of the amino acid sequence contains a characteristic difference in amino acid sequence that defines HD-ZIPIII proteins as belonging to the REVOLUTA or non-REVOLUTA classes of proteins. The boxed portion of the sequences indicate the site of the amino acid sequence insertion that defines non-REVOLUTA HD-ZIPIII proteins. REVOLUTA proteins are defined by the lack of an amino acid sequence insertion. Athb-9 (*Arabidopsis*; SEQ ID NO:2); Athb-14 (*Arabidopsis*; SEQ ID NO:3); REV (*Arabidopsis*; SEQ ID NO:4); BnLfREV (*Brassica napus*; SEQ ID NO:5); OsREV1 (*Oryza sativa*; SEQ ID NO:6); ZmRLD1 (*Zea mays*; SEQ ID NO:7); OsREV2 (*Oryza sativa*; SEQ ID NO:8); Athb-15 (*Arabidopsis*; SEQ ID NO:9); and Athb-8 (*Arabidopsis*; SEQ ID NO:10).

DETAILED DESCRIPTION OF THE INVENTION

Figure 1:
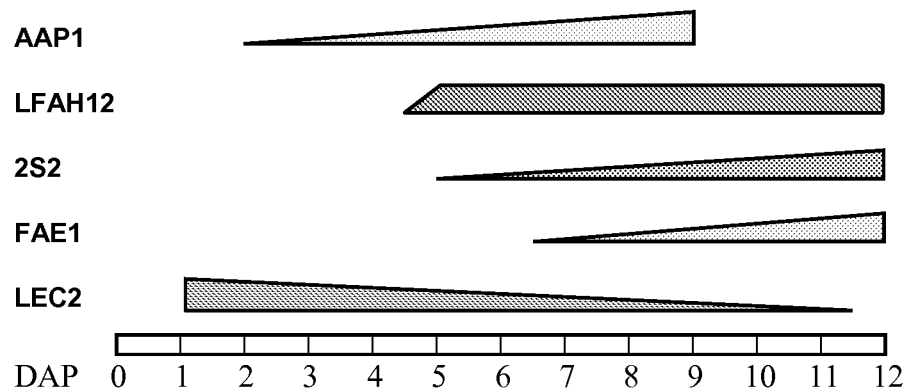
FIG. 1 depicts the expression profiles of embryo-specific promoters during early embryo development. Approximate stages in *Arabidopsis* embryo development: early globular=2 days after pollination (DAP), heart=4 DAP, torpedo=6 DAP, walking stick=7 DAP, early maturation embryo=8 DAP.

The present invention provides methods and compositions useful for producing plants having an increased seed size and/or increased seed number when compared to a wild-type plant. In particular, the methods comprise over expression of a gene involved in plant growth and/or development in an embryo of a plant wherein the over expression of the transgene results in an increase in seed size and/or an increased number of seeds in the plant. In a particular embodiment the REVOLUTA (REP) gene was overexpressed. The REV transgene in the methods of the present invention is under the regulation of a promoter that initiates expression during embryo development and in particular initiates expression during early phase-specific embryo development. Unexpectedly, over expression of the REV transgene in early stage embryo development resulted in larger and/or more seeds.

As a first attempt to determine if seed size could be increased through over expression of a gene involved in plant growth and/or development the REV gene was targeted to the seed, a REV transgene construct comprising an embryo-specific promoter to drive REV expression was tested. The availability of a number of embryo-specific promoters with well characterized expression profiles during *Arabidopsis* embryo development made it possible to create transgenic plants in which REV over expression was targeted to several different but overlapping phases of embryo development. The *Arabidopsis* REV transgene constructs were introduced into canola for testing. The rationale for going directly to canola was that the *Arabidopsis* genome is very closely related to canola so the known expression characteristics of the promoters as determined in *Arabidopsis* would likely carry over to canola and that canola is a crop species. Demonstration of an effect on seed size in canola would have direct agricultural relevance.

As used herein, a plant growth and/or development related gene is a gene that plays a role in determining growth rate, overall size, tissue size, or tissue number of a plant or plays a role in the plant developmental program leading to determination of tissue identity and morphology. Such growth and development related genes are identified when modification of their function by mutation, overexpression, or suppression of expression results in altered plant growth rate, overall plant size, tissue size or number, or altered development. Plant and growth related genes can exert their effects through a number of mechanisms some of which include regulation of cell cycle, plant hormone synthesis/breakdown pathways, sensitivity to plant hormones, cell wall biosynthesis, cell identity determination, and the like.

A number of plant genes have been shown by overexpression or suppression analysis to play roles in growth and/or development. Examples of some, but not all, of the genes that are known to be involved in growth and/or development and that can be used or tested in the methods of the present invention are discussed herein below. The *Arabidopsis* CAP gene encodes a cyclase-associated protein that is involved in Ras-cAMP signaling and regulation of the actin cytoskeleton. Overexpression of CAP under a glucocorticoid-inducible promoter causes a loss of actin filaments and a reduction in the size of leaves due to reduced elongation of epidermal and mesophyll cells (Barrero et al., *Annals of Botany* 91:599-603, 2003). Suppression of sucrose synthase gene expression in cotton leads to reduced cell fiber length and smaller and fewer fiber cells (Yong-Ling Ruan et al., *Plant Cell* 15:952-964, 2003). Overexpression of the rice histone deacetylase 1 gene with an ABA-inducible promoter in transgenic rice resulted in plants with an increase in growth rate and abnormal shoot and root tissue development compared to the wild-type (In-Cheol Jang et al, *Plant J.* 33:531-541, 2003). Suppression of E2Fc by RNAi in *Arabidopsis* increases proliferative activity in leaves, meristems, and pericycle cells. Cells in organs were smaller but more numerous than wild type and there was a reduced ploidy level in the leaves (del Pozo et al., *Plant Cell* 18:2224-2235, 2006). Suppression of the BKI gene by RNAi resulted in seedlings with increased hypocotyls lengths and overexpression of BKI gaves dwarf plants (Xuelu and Chory, *Science* 313:1118-1122, 2006). Transgenic plants expressing a partially constitutive steroid receptor BRI1 have longer hypocotyls (Wang et al, *Dev. Cell* 8:855-865, 2005). Suppression of Argos-Like (ARL) in *Arabidopsis* gave smaller cotyledons, leaves and other lateral organs, while overexpression gave the opposite effect. The change in organ size can be attributed to cell size rather than to cell number (Hu et al., *Plant J.* 47:1-9, 2006).

Analysis of plants with mutations resulting in altered growth and/or developmental phenotypes has identified a number of genes that play roles in plant growth and development. A mutation affecting brassinosteroid hormone perception, bri1-5, results in a dwarf plant (Wang et al., *Dev. Cell* 8:855-865, 2005). A T-DNA insertion (a knock-out) in the *Arabidopsis* FATB gene encoding an acyl-acyl carrier protein thioesterase leads to reduced growth rate, reduced fresh weight and low seed viability (Bonaventure et al., *Plant Cell* 15:1020-1033, 2003). A loss-of-function mutation in Pepino, a putative anti-phosphatase, displayed tumor-like cell proliferation at the shoot apical meristem and produced supernumerary abnormal leaves (Haberer et al., *Dev. Genes Evol.* 212:542-550, 2002). The *Arabidopsis* RGS gene (regulator of G protein signaling) has the structure of a G-protein-coupled receptor (GPCR) and contains an RGS box. RGS proteins accelerate the deactivation of the Gα subunit and thus reduce GPCR signaling. The null rgs mutant has increased cell elongation in hypocotyls grown in the dark and increased cell production in roots grown in light (Chen et al., *Science* 301:1728-1731, 2003). The *Arabidopsis* TIP1 gene plays a role in root hair development and also in cellular growth. The tip1-2 mutant has smaller rosettes, reduced height and shorter internodes (Ryan et al., *New Phytol.* 138:49-58, 1998 and Hemsley et al., *Plant Cell* 17:2554-2563, 2005). Mutants (chromosomal rearrangement or T-DNA insertion) of the Big Brother (BB) gene that give very little or no Big Brother mRNA develop larger floral organs, more flower biomass and thicker stems. Conversely, overexpression of Big Brother leads to smaller floral organs, less flower biomass, thinner stems and reduced leaf size. BB may be altering cell number (Disch et al., Curr. Biol. 16:272-279, 2006). The RHD2 gene encodes an NADPH oxidase important for accumulation of reactive-oxygen species in root hairs and the subsequent activation of calcium channels. The rhd2 mutant is defective in cell expansion of the tip growing cells of the root (Foreman et al., Nature 422:442-446, 2003). The miniature mutation in maize causes a loss in the cell wall invertase, expressed from the INCW2 gene. Cells of the mn1 mutant are smaller than wild-type and mn1 seed mutants only have 20% of the endosperm weight of wild type seeds. Expansion may be compromised in cells of the peripheral layers of the mn1 endosperm and may lead to decreased mitotic activity of these cells (Vilhar et al., Plant Physiol. 129: 23-30, 2002). A T-DNA insertion mutant of WAK2, wak2-1, has decreased cell elongation in roots. WAK2 may control cell expansion through regulation of vacuolar invertase activity. Expression of an inducible antisense of WAK2 or WAK4 in plants prevents cell elongation and produces dwarf plants (Wagner and Kohorn, Plant Cell 13:303-318, 2001, Lally et al., Plant Cell 13:1317-1331, 2001, and Kohorn et al., Plant J. 46:307-316, 2006). The Arabidopsis gene AP2 plays a role in floral organ identity and establishment of floral meristem identity. Loss-of-function mutations in AP2 gives increased seed mass compared to the wild type (Masa-Ohto et al., Proc. Nat'l. Acad. Sci. USA 102:3123-3128, 2005). teb mutants have short roots, serrated leaves, and fasciation. They show defects in cell division that may be caused by a defect in G2/M cell cycle progression (Inagaki et al., Plant Cell 18:879-892, 2006).

The terms "growth and/or development gene" or "growth and/or development transgene" are used herein to mean any polynucleotide sequence that encodes or facilitates the expression and/or production of a nucleotide or protein encoded by the gene. Thus the terms "growth and/or development gene" or "growth and/or development transgene" can include sequences that flank the nucleotide and/or protein encoding sequences. For example, the sequences can include those nucleotide sequences that are protein encoding sequences (exons), intervening sequences (introns), the flanking 5' and 3' DNA regions that contain sequences required for normal expression of the gene (i.e., the promoter and polyA addition regions, respectively, and any enhancer sequences).

The terms "growth and/or development protein," "growth and/or development homolog" or "growth and/or development associated ortholog" are used herein to mean protein having the ability to regulate growth rate, overall size, tissue size, or tissue number of a plant or regulate the plant developmental program leading to determination of tissue identity and morphology (when utilized in the practice of the methods of the present invention) and that have an amino acid sequence that is at least about 70% identical, more typically at least about 75% identical, and more typically at least about 80% identical to the amino acid sequences for the gene.

As used herein an "embryo-specific gene" is a gene that is preferentially expressed during embryo development in a plant. For purposes of the present disclosure, embryo development begins with the first cell divisions in the zygote and continues through the late phase of embryo development (characterized by maturation, desiccation, dormancy), and ends with the production of a mature and desiccated seed. Embryo-specific genes can be further classified as "early phase-specific" and "late phase-specific". Early phase-specific genes are those expressed in embryos up to the end of embryo morphogenesis. Late phase-specific genes are those expressed from maturation through to production of a mature and desiccated seed. Examples of embryo-specific genes that initiate expression during early embryo development and are early phase-specific are presented in FIG. 1.

A "heterologous sequence" is an oligonucleotide sequence that originates from a different species, or, if from the same species, is substantially modified from its original form. For example, a heterologous promoter operably linked to a structural gene is from a species different from that from which the structural gene was derived, or, if from the same species, is substantially modified from its original form.

The term "vector" refers to a piece of DNA, typically double-stranded, which may have inserted into it a piece of foreign DNA. The vector or replicon may be for example, of plasmid or viral origin. Vectors contain "replicon" polynucleotide sequences that facilitate the autonomous replication of the vector in a host cell. The term "replicon" in the context of this disclosure also includes polynucleotide sequence regions that target or otherwise facilitate the recombination of vector sequences into a host chromosome. In addition, while the foreign DNA may be inserted initially into, for example, a DNA virus vector, transformation of the viral vector DNA into a host cell may result in conversion of the viral DNA into a viral RNA vector molecule. Foreign DNA is defined as heterologous DNA, which is DNA not naturally found in the host cell, which, for example, replicates the vector molecule, encodes a selectable or screenable marker or transgene. The vector is used to transport the foreign or heterologous DNA into a suitable host cell. Once in the host cell, the vector can replicate independently of or coincidental with the host chromosomal DNA, and several copies of the vector and its inserted DNA can be generated. Alternatively, the vector can target insertion of the foreign or heterologous DNA into a host chromosome. In addition, the vector can also contain the necessary elements that permit transcription of the inserted DNA into a mRNA molecule or otherwise cause replication of the inserted DNA into multiple copies of RNA. Some expression vectors additionally contain sequence elements adjacent to the inserted DNA that allow translation of the mRNA into a protein molecule. Many molecules of mRNA and polypeptide encoded by the inserted DNA can thus be rapidly synthesized.

The term "transgene vector" refers to a vector that contains an inserted segment of DNA, the "transgene," that is transcribed into mRNA or replicated as a RNA within a host cell. The term "transgene" refers not only to that portion of inserted DNA that is converted into RNA, but also those portions of the vector that are necessary for the transcription or replication of the RNA. In addition, a transgene need not necessarily comprise a polynucleotide sequence that contains an open reading frame capable of producing a protein.

The terms "transformed host cell," "transformed," and "transformation" refer to the introduction of DNA into a cell. The cell is termed a "host cell," and it may be a prokaryotic or a eukaryotic cell. Typical prokaryotic host cells include various strains of E. coli. Typical eukaryotic host cells are plant cells (e.g., canola, cotton, camelina, alfalfa, soy, rice, oat, wheat, barley, or corn cells, and the like), yeast cells, insect cells, or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

The term "plant" includes whole plants, plant organs, (e.g., leaves, stems, flowers, roots, and the like), seeds and plant cells (including tissue culture cells) and progeny of same. The class of plants which can be used in the methods of the present invention is generally as broad as the class of higher plants amenable to transformation techniques, including both monocotyledonous and dicotyledonous plants, as well as certain lower plants such as algae. It includes plants of a variety of ploidy levels, including polyploidy, diploid and haploid.

A "heterologous sequence" is one that originates from a foreign species, or, if from the same species, is substantially modified from its original form. For example, a heterologous promoter operably linked to a structural gene is from a species different from that from which the structural gene was derived, or, if from the same species, is substantially modified from its original form.

The terms "REVOLUTA gene" or "REVOLUTA transgene" are used herein to mean any polynucleotide sequence that encodes or facilitates the expression and/or production of a REVOLUTA protein. Thus the terms "REVOLUTA gene" or "REVOLUTA transgene" can include sequences that flank the REVOLUTA protein encoding sequences. For example, the sequences can include those nucleotide sequences that are protein encoding sequences (exons), intervening sequences (introns), the flanking 5' and 3' DNA regions that contain sequences required for normal expression of the REVOLUTA gene (i.e., the promoter and polyA addition regions, respectively, and any enhancer sequences).

The terms "REVOLUTA protein," "REVOLUTA homolog" or "REVOLUTA ortholog" are used herein to mean protein having the ability to regulate plant cell division (when utilized in the practice of the methods of the present invention) and that have an amino acid sequence that is at least about 70% identical, more typically at least about 75% identical, and more typically at least about 80% identical to the amino acid sequences for REVOLUTA described in WO 01/33944 (incorporated herein by reference in its entirety).

Alternatively, the terms "REVOLUTA protein" "REVOLUTA homolog", or "REVOLUTA ortholog" are used herein to mean REVOLUTA proteins that are identified as distinct from non-REVOLUTA members of the HD-ZIPIII class of plants transcription factors. The REVOLUTA members of the HD-ZIPIII class of proteins are characterized by the lack or absence of a characteristic amino acid sequence insertion that is present in non-REVOLUTA HD-ZIPIII proteins between amino acid residues 146 and 147 of the REVOLUTA amino acid sequence described in WO 01/33944 and as shown in FIG. 2. In FIG. 2, Homeobox transcription factors from *Arabidopsis thaliana* designated athb-8, athb-9, athb-14 and athb-15 are non-REVOLUTA HD-ZIPIII proteins and all have a characteristic amino acid sequence insertion between amino acids 146 and 147 of the REVOLUTA amino acid sequence. The five REVOLUTA sequences in FIG. 2, all lack an amino acid insertion at this location in the REVOLUTA amino acid sequence. The lack of this amino acid sequence insertion is a distinguishing and defining characteristic of REVOLUTA proteins.

The term "percent identity" means the percentage of amino acids or nucleotides that occupy the same relative position when two amino acid sequences, or two nucleic acid sequences are aligned side by side using a computer program such as one identified below. The term "percent similarity" is a statistical measure of the degree of relatedness of two compared protein sequences. The percent similarity is calculated by a computer program that assigns a numerical value to each compared pair of amino acids based on chemical similarity (e.g., whether the compared amino acids are acidic, basic, hydrophilic, aromatic, and the like) and/or evolutionary distance as measured by the minimum number of base pair changes that would be required to convert a codon encoding one member of a pair of compared amino acids to a codon encoding the other member of the pair. Calculations are made after a best fit alignment of the two sequences has been made empirically by iterative comparison of all possible alignments. (See for example, Henikoff et al., *Proc. Natl. Acad. Sci. USA* 89:10915-10919, 1992).

The term "substantial identity" of poly nucleotide sequences means that a polynucleotide comprises a sequence that has at least 60% sequence identity, typically at least 70%, more typically at least 80% and most typically at least 90%, compared to a reference sequence using the programs described below using standard parameters. One of skill will recognize that these values can be appropriately adjusted to determine corresponding identity of proteins encoded by two nucleotide sequences by taking into account codon degeneracy, amino acid similarity, reading frame positioning and the like.

Amino acid sequence identity can be determined, for example, in the following manner. The portion of the amino acid sequence of the protein encoded by the growth and/or development associated gene, e.g., REVOLUTA, can be used to search a nucleic acid sequence database, such as the GenBank® database, using the program BLASTP version 2.0.9 (Atschul et al., *Nucl. Acids Res.* 25:3389-3402, 1997). Sequence comparisons between two (or more) polynucleotides or polypeptides are typically performed by comparing sequences of the two sequences over a "comparison window" to identify and compare local regions of sequence similarity. A "comparison window" as used herein refers to a segment of at least about 20 contiguous positions, usually about 50 to about 200, more usually about 100 to about 150 in which a sequence can be compared to a reference sequence of the same number of contiguous positions after the two sequences are optimally aligned.

Optimal alignment of sequence for comparison can be conducted by local identity or similarity algorithms such as those described in Smith et al., *Adv. Appl. Math.* 2:482, 1981, by the homology alignment algorithm of Needleman et al., *J. Mol. Biol.* 48:443-453, 1970, by the search for similarity method of Pearson et al., *Proc. Natl. Acad. Sci. USA* 85:2444-2448, 1988, by computerized implementations of these algorithms (GAP, BESTFIT, FASTA, and TFASTA in the Wisconsin Genetics Software Package, Genetics Computer Group, 575 Science Drive, Madison, Wis.), or by visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng et al. *J. Mol. Evol.* 35:351-360, 1987. The method used is similar to the method described by Higgins et al., *CABIOS* 5:151-153, 1989. The program can align up to 300 sequences, each of a maximum length of 5,000 nucleotides or amino acids. The multiple alignment procedure begins with the pairwise alignment of the two most related sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their nucleotide or amino acid coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul et al., *J. Mol. Biol.* 215:403-410, 1990. Software for performing BLAST analyses is publicly available through the National Center for Biotechnology Information web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as for as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and the speed of the alignment. The BLAST program uses as defaults a wordlength (W) of 11, the BLOSUM62 scoring matrix (see, Henikoff et al, *Proc. Natl. Acad. Sci. USA* 89:10915-10919, 1992) alignments (B) of 50, expectation (E) of 10, M=5, N=−4, and a comparison of both strands.

In addition to calculating percent sequence identity, the BLAST algorithm also performs statistical analysis of the similarity between two sequences (see e.g., Karlin et al., *Proc. Natl. Acad. Sci. USA* 90:5873-5877, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison test is less than about 0.1, more preferably less than about 0.01, and most preferably less than about 0.001. Additional methods and algorithms for sequence alignment and analysis of sequence similarity are well known to the skilled artisan.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "growth and/or development gene" and "growth and/or development transgene", and specifically "REVOLUTA gene" and "REVOLUTA transgene". In addition, these terms specifically include those full length sequences substantially identical with a gene sequence and that encode a protein that retains the function of the gene product, e.g., REVOLUTA. Two nucleic acid sequences or polynucleotides are said to be "identical" if the sequences of nucleotides or amino acid residues, respectively, in the two sequences is the same when aligned for maximum correspondence as described above. The term "complementary to" is used herein o mean that the complementary sequence is identical to all or a portion of a reference polynucleotide sequence.

Variations and alterations in the amino acid sequence of the growth and/or development associated gene and growth and/or development associated protein, e.g., the REVOLUTA gene and REVOLUTA protein sequences are described in WO 01/33944, incorporated herein by reference. The gene of interest, such as the REVOLUTA gene, polynucleotide or polynucleotide sequence can be isolated from or obtained from any plant species. In a particular embodiment of the present invention the REVOLUTA gene sequence used is that from *Arabidopsis thaliana*, but the REVOLUTA gene from other species of interest can also be used. For example the nucleotide sequence and amino acid sequence for REVOLUTA from corn (*Zea mays*) is described in WO 2004/063379 (incorporated herein by reference in its entirety).

The terms "biological activity", "biologically active", "activity", "active", "biological function", "REV biological activity", and "functionally active" refer to the ability of the protein of interest, such as REVOLUTA proteins to dimerize (or otherwise assemble into protein oligomers), or the ability to modulate or otherwise effect the dimerization of native wild-type (e.g., endogenous) REVOLUTA protein. However, the terms are also intended to encompass the ability of a protein of interest, such as the REVOLUTA proteins, to bind and/or interact with other molecules, including for example, but not by limitation, DNA containing specific nucleotide sequences in promoter regions recognized by the protein, e.g., the REVOLUTA protein, and which binding and/or interaction events(s) mediate plant cell division and ultimately confer a phenotype, or the ability to modulate or otherwise effect the binding and/or interaction of other molecules with native wild-type protein and which binding and/or interaction event(s) mediate plant cell division and ultimately confer a phenotype associated with the gene of interest.

REV phenotype as used herein is intended to refer to a phenotype conferred by a REV nucleic acid or protein and particularly encompasses the characteristic wherein the seed size or seed number is exhibited. Typically, a REV phenotype is determined by examination of a plant over expressing REV during early phase-specific embryo development, where the number and size of seeds from the plant can be compared to the number and size of seeds in the corresponding tissues of a parental or wild-type plant. Plants having the REV phenotype have a statistically significant change in the number and/or size of the seeds within a representative number of a plant population.

A promoter suitable for being operably linked to a plant growth and/or development associated gene and expressed using the described methods of the present invention typically has greater expression in embryo and lower or no expression in other plant tissues. Of particular interest are those promoter sequences that initiate expression in early phase-specific embryo development. An early phase-specific promoter is a promoter that initiates expression of a protein prior to day 7 after pollination (walking stick) in *Arabidopsis* or an equivalent stage in another plant species. Examples of promoter sequences of particular interest include a promoter for the amino acid permease gene (AAP1) (e.g., the AAP1 promoter from *Arabidopsis thaliana*) (Hirner et al., *Plant J.* 14:535-544, 1998), a promoter for the oleate 12-hydroxylase:desaturase gene (e.g., the promoter designated LFAH12 from *Lesquerella fendleri*) (Broun et al., *Plant J.* 13:201-210, 1998), a promoter for the 2S2 albumin gene (e.g., the 2S2 promoter from *Arabidopsis thaliana*) (Guerche et al., *Plant cell* 2:469-478, 1990), a fatty acid elongase gene promoter (FAE1) (e.g., the FAE1 promoter from *Arabidopsis thaliana*) (Rossak et al., *Plant Mol. Biol.* 46:717-715, 2001), and the leafy cotyledon gene promoter (LEC2) (e.g., the LEC2 promoter from *Arabidopsis thaliana*)(Kroj et al. *Development* 130:6065-6073, 2003). Other early embryo-specific promoters of interest include, but are not limited to, Seedstick (Pinyopich et al., *Nature* 424:85-88, 2003), Fbp7 and Fbp11

(Petunia Seedstick) (Colombo et al., *Plant Cell.* 9:703-715, 1997), Banyuls (Devic et al., *Plant J.* 19:387-398, 1999), agl-15 and agl-18 (Lehti-Shiu et al., *Plant Mol. Biol.* 58:89-107, 2005), Phe1 (Kohler et al., *Genes Develop.* 17:1540-1553, 2003), Per1 (Haslekas et al., *Plant Mol Biol.* 36:833-845, 1998; Haslekas et al., *Plant Mol. Biol.* 53:313-326, 2003), emb175 (Cushing et al., *Planta* 221:424-436, 2005), L11 (Kwong et al., *Plant Cell* 15:5-18, 2003), Lec1 (Lotan et al., *Cell* 93:1195-1205, 1998), Fusca3 (Kroj et al., *Development* 130:6065-6073, 2003), tt12 (Debeaujon et al., *Plant Cell* 13:853-871, 2001), tt16 (Nesi et al., *Plant Cell* 14:2463-2479, 2002), A-RZf (Zou and Taylor, *Gene* 196:291-295, 1997), TtG1 (Walker et al., *Plant Cell* 11:1337-1350, 1999; Tsuchiya et al., *Plant J.* 37:73-81, 2004), Tt1 (Sagasser et al., *Genes Dev.* 16:138-149, 2002), TT8 (Nesi et al., *Plant Cell* 12:1863-1878, 2000), Gea-8 (carrot) (Lin and Zimmerman, J. Exp. Botany 50:1139-1147, 1999), Knox (rice) (Postma-Haarsma et al., *Plant Mol. Biol.* 39:257-271, 1999), Oleosin (Plant et al., *Plant Mol. Biol.* 25:193-205, 1994; Keddie et al., *Plant Mol. Biol.* 24:327-340, 1994), AB13 (Ng et al., *Plant Mol. Biol.* 54:25-38, 2004; Parcy et al., *Plant Cell* 6:1567-1582, 1994), and the like.

The promoters suitable for use in the present invention can be used either from the same species of plant to be transformed or can be from a heterologous species. Further, the promoter can be from the same species as for the REV transgene to be used or it can be from a heterologous species. Promoters for use in the methods of the present invention can also comprise a chimeric promoter which can include a combination of promoters that have an expression profile in common with one or more of those described above. In one embodiment of the present invention, the AAP1 gene promoter from *Arabidopsis thaliana* was combined with the *Arabidopsis thaliana* REV gene and used to construct transgenic canola (*Brassica napus*). Further, in an additional embodiment of the present invention the oleate 12-hydroxylase:desaturase gene promoter LFAH12 from *Lesquerella fendleri* was operatively linked to the *Arabidopsis thaliana* REV gene and used to construct transgenic canola (*Brassica napus*). Each of the above transgenic plants demonstrated the REV phenotype characteristic of the methods of the present invention wherein REV is over expressed in early embryo development resulting in increased seed size and/or seed number.

It should be noted that the early phase-specific promoters described above are only representative promoters that can be used in the methods of the present invention. Methods for identifying and characterizing promoter regions in plant genomic DNA are well known to the skilled artisan and include, for example, those described by Jordano et al., *Plant Cell* 1:855-866, 1989; Bustos et al., *Plant Cell* 1:839-854, 1989; Green et al., *EMBO J.* 7:4035-4044, 1988; Meier et al., *Plant Cell* 3:309-316, 1991; and Zhang et al, *Plant Physiol.* 110:1069-1079, 1996.

Transgenic plants which over express REV in early phase embryos can be obtained, for example, by transferring transgenic vectors (e.g., plasmids, virus, and the like) that encode an early phase-specific embryo promoter operatively linked to a gene that encodes REVOLUTA into a plant. Typically, when the vector is a plasmid the vector also includes a selectable marker gene, e.g., the kanamycin gene encoding resistance to kanamycin. The most common method of plant transformation is performed by cloning a target transgene into a plant transformation vector that is then transformed into *Agrobacterium tumifaciens* containing a helper Ti-plasmid as described in Hoeckeme et al., (*Nature* 303:179-181, 1983). Additional methods are described in for example, Maloney et al., *Plant Cell Reports* 8:238, 1989. The *Agrobacterium* cells containing the transgene vector can be incubated with leaf slices of the plant to be transformed as described by An et al. (*Plant Physiol.* 81:301-305, 1986; Hooykaas, *Plant Mol. Biol.* 13:327-336, 1989). Transformation of cultured plant host cells is typically accomplished through *Agrobacterium tumifaciens*, as described above. Cultures of host cells that do not have rigid cell membrane barriers are usually transformed using the calcium phosphate method as originally described by Graham et al. (*Virology* 52:546, 1978) and modified as described in Sambrook et al. (*Molecular Cloning: A Laboratory Manual* (2nd Ed., 1989 Cold Spring Harbor Laboratory Press, New York, N.Y.). However, other methods for introducing DNA into cells such as Polybrene (Kawai et al., *Mol. Cell. Biol.* 4:1172, 1984), protoplast fusion (Schaffner, *Proc. Natl. Acad. Sci. USA* 77:2163, 1980), electroporation (Neumann et al., *EMBO J.* 1:841, 1982), and direct microinjection into nuclei (Capecchi, *Cell* 22:479, 1980) can also be used. Transformed plant calli can be selected through the selectable marker by growing the cells on a medium containing, e.g., kanamycin, and appropriate amounts of phytohormone such as naphthalene acetic acid and benzyladenine for callus and shoot induction. The plant cells can then be regenerated and the resulting plants transferred to soil using techniques well known to those skilled in the art.

In addition to the methods described above, a large number of methods are well known in the art for transferring cloned DNA into a wide variety of plant species, including gymnosperms, angiosperms, monocots and dicots (see, e.g., Glick and Thompson, eds., *Methods in Plant Molecular Biology and Biotechnology*, CRC Press, Boca Raton, Fla., 1993; Vasil, *Plant Mol. Biol.*, 25:925-937, 1994; and Komai et al., *Current Opinions Plant Biol.* 1:161-165, 1998 (general review); Loopstra et al., *Plant Mol. Biol.* 15:1-9, 1990; and Brasileiro et al., *Plant Mol. Biol.* 17:441-452, 1990 (transformation of trees); Eimert et al., *Plant Mol. Biol.* 19:485-490, 1992 (transformation of *Brassica*); Hiei et al., *Plant J.* 6:271-282, 1994; Hiei et al., *Plant Mol. Biol.* 35:205-218, 1997; Chan et al., *Plant Mol. Biol.* 22:491-506, 1993; U.S. Pat. Nos. 5,516,668 and 5,824,857 (rice transformation); and U.S. Pat. No. 5,955,362 (wheat transformation); U.S. Pat. No. 5,969,213 (monocot transformation); U.S. Pat. No. 5,780,798 (corn transformation); U.S. Pat. Nos. 5,959,179 and 5,914,451 (soybean transformation). Representative examples include electroporation-facilitated DNA uptake by protoplasts (Rhodes et al., *Science* 240:204-207, 1988; Bates, *Meth. Mol Biol.* 111:359-366, 1999; D'Halluin et al., *Meth. Mol. Biol.* 111:367-373, 1999; U.S. Pat. No. 5,914,451); treatment of protoplasts with polyethylene glycol (Lyznik et al., *Plant Mol. Biol.* 13:151-161, 1989; Datta et al., *Meth. Mol. Biol.*, 111:335-334, 1999); and bombardment of cells with DNA laden microprojectiles (Klein et al., *Plant Physiol.* 91:440-444, 1989; Boynton et al., *Science* 240:1534-1538, 1988; Register et al., *Plant Mol. Biol.* 25:951-961, 1994; Barcelo et al., *Plant J.* 5:583-592, 1994; Vasil et al., *Meth. Mol. Biol.* 111:349-358, 1999; Christou, *Plant Mol. Biol.* 35:197-203, 1997; Finer et al., *Curr. Top. Microbiol. Immunol.* 240:59-80, 1999). Additionally, plant transformation strategies and techniques are reviewed in Birch, *Ann. Rev. Plant Phys. Plant Mol. Biol.* 48:297, 1997; Forester et al., *Exp. Agric.* 33:15-33, 1997. Minor variations make these technologies applicable to a broad range of plant species.

In the case of monocot transformation, particle bombardment is typically the method of choice. However, monocots such as maize can also be transformed by using *Agrobacterium* transformation methods as described in U.S. Pat. No. 5,591,616. Another method to effect monocot transformation, e.g., corn, mixes cells from embryogenic suspension cultures with a suspension of fibers (5% w/v, Silar SC-9 whiskers) and plasmid DNA (1 µg/ul) and which is then placed either upright in a multiple sample head on a Vortex GENIE II vortex mixer (Scientific Industries, Inc., Bohemia, N.Y., USA) or horizontally in the holder of a MIXOMAT dental amalgam mixer (Degussa Canada Ltd., Burlington, Ontario, Canada). Transformation can then be carried out by mixing at full speed for about 60 seconds (for example with a Vortex GENIE II) or shaking at fixed speed for 1 second (MIXOMAT). This process results in the production of cell populations out of which stable transformants can be selected. Plants are regenerated from the stably transformed calluses and these plants and their progeny can be shown by Southern hybridization analysis to be transgenic. The principal advantages of the approach are its simplicity and low cost. Unlike particle bombardment, expensive equipment and supplies are not required. The use of whiskers for the transformation of plant cells, particularly maize, is described in, for example, U.S. Pat. No. 5,464,765.

U.S. Pat. No. 5,968,830 describes methods of transforming and regenerating soybean. U.S. Pat. No. 5,969,215 describes transformation techniques for producing transformed *Beta vulgaris* plants, such as the sugar beet.

Each of the above transformation techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest.

Traditional *Agrobacterium* transformation with antibiotic resistance selectable markers can be problematical because of public opposition that such plants pose an undue risk-of spreading antibiotic tolerance to animals and humans. Such antibiotic markers can be eliminated from plants by transforming plants using the *Agrobacterium* techniques similar to those described in U.S. Pat. No. 5,731,179. Antibiotic resistance issues can also be effectively avoided by the use of bar or pat coding sequences, such as is described in U.S. Pat. No. 5,712,135. These preferred marker DNAs encode second proteins or polypeptides inhibiting or neutralizing the action of glutamine synthetase inhibitor herbicides phosphinothricin (glufosinate) and glufosinate anunonium salt (Basta, Ignite).

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

There are numerous factors that influence the success of transformation. The design and construction of the exogenous gene construct and its regulatory elements influence the integration of the exogenous sequence into the chromosomal DNA of the plant nucleus and the ability of the transgene to be expressed by the cell. A suitable method for introducing the exogenous gene construct into the plant cell nucleus in a non-lethal manner is essential. Importantly, the type of cell into which the construct is introduced must, if whole plants are to be recovered, be of a type which is amenable to regeneration, given an appropriate regeneration protocol.

Prokaryotes can also be used as host cells for the initial cloning steps of the present invention. Methods, vectors, plasmids and host cell systems are well known to the skilled artisan that can be used for these initial cloning and expansion steps and will not be described herein.

In another embodiment of the present invention an early phase-specific embryo promoter can be inserted so as to be operatively linked to a gene encoding a plant growth and/or development associated gene, such REV, in the plant to be transformed using methods well known to the skilled artisan. Insertion of the promoter will allow for the early embryonic expression of the gene, e.g., REV, in the developing seeds of the transgenic plant.

Transgenic plants of particular interest in the methods of the present invention include but are not limited to monocot and dicots particularly from the families Brassicacea (Cruciferae), Gramineae, Malvaceae, or Leguminosae-Papilionoideae. Plants of particular interest within these families include, but are not limited to canola, corn, camelina cotton, wheat, rice, soybean, barley and other seed producing plants, as well as other plants including, but not limited to alfalfa, and the like, of agricultural interest which comprise in a particular embodiment of the present invention, a REV transgene under the control of an early phase-specific embryo promoter. The transgene can be from the same species as the transgenic plant, or the transgene can be from a heterologous plant. Of particular interest is a transgenic plant comprising the REV transgene from *Arabidopsis*. The early phase-specific embryo promoter can also be from the same species as the transgenic plant, or from a heterologous plant. For example, the early phase-specific embryo promoter can be from the same plant species as the REV transgene or even from another species of plant. Of particular interest are early phase-specific embryo promoters from *Arabidopsis* or *Lesquerella fendleri*, but the early phase-specific promoter can be obtained from another species of plant. Specific combinations of early phase-specific promoter and REV transgene that have been found to be suitable for the methods of the present invention include, but are not limited to (a) *Lesquerella fendleri* LFAH12 promoter/*Arabidopsis* REV; (b) *Arabidopsis* AAP1 promoter/*Arabidopsis* REV; (c) *Arabidopsis* LEC2 promoter/*Arabidopsis* REV; and (d) *Arabidopsis* 2S2 promoter/*Arabidopsis* REV. In a particular embodiment of the present invention, these transgene constructs have been used to transform canola, but can be used to transform other plant species. In particular, they can be used to produce transgenic plants having increased seed size and/or seed number in soybeans, corn, cotton, camelina, rice, wheat, barley, alfalfa, and other crops of agricultural interest.

The present invention also provides methods for selecting a growth and/or development associated gene that increases plant yield. In the method, a gene of interest is functionally associated with an early phase-specific embryo promoter in an expression plasmid or vector. The expression plasmid or vector comprising the gene of interest is transfected into a plant cell using a method known in the art to form a transgenic cell. The cell comprising the transgene is grown up and regenerated into a transgenic plant by known methods, including those disclosed above until transgenic plants are obtained. The transgenic plants are observed for increased yield as compared with a wild-type plant and those growth and/or development associated genes that were used to obtain the transgenic plants with increased yield are selected for further development. Transgenic plants comprising the selected growth and/or development associated gene can be further developed to provide plants of agricultural importance with a higher yield than the wild-type plants.

The following examples are provided merely as illustrative of various aspects of the invention and shall not be construed to limit the invention in any way.

EXAMPLES

The following example describes the construction of various expression vectors comprising a early phase-specific embryo promoter and a gene with a role in plant growth and/or development. In particular, the embryo specific promoters (a) *Lesquerella fendleri* LFAH12; (b) *Arabidopsis* AAP1; (c) *Arabidopsis* LEC2; (d) *Arabidopsis* 2S2, and (e) *Arabidopsis* FAE1 were operatively associated with the *Arabidopsis* REVOLUTA (REV) gene and used to produce transgenic canola plants.

Example 1

Transgenic Canola Plants Expressing Transgene Constructs Designed to Confer Embryo-Specific Expression of REVOLUTA Constitutive over-expression of the *Arabidopsis* REV gene in transgenic *Arabidopsis* plants results in increased seed size relative to non-transgenic wild type *Arabidopsis* plants, but this trait is accompanied by negative pleiotropic effects. These effects include altered leaf morphology and reduced axillary shoot formation in *Arabidopsis*. Altered leaf morphology and overall stunted growth of plants are negative effects observed in transgenic canola over-expressing the REV gene at high constitutive levels throughout the plant. To obtain the increased seed size trait while avoiding undesirable effects in non-seed tissues, a strategy can be taken to target over-expression of the REV transgene specifically to the developing embryo in the seed. This can be accomplished using a transgene expression construct in which an embryo-specific promoter drives the expression of the REV gene. Constitutive overexpression of other plant genes like REV involved in plant development and growth processes could also be reasonably expected to have negative pleiotropic effects on the transgenic plant. The use of embryo-specific promoters to evaluate plant genes that have roles in development and growth as possible yield enhancing genes offers a general approach to evaluate such plant genes for efficiency in increasing crop yield.

Five promoters that confer embryo-specific expression were selected for use in expression constructs designed to give transgenic expression of REV in canola embryos (*Brassica napus*) during early embryo development. These promoters include AAP1 (amino acid permease gene from *Arabidopsis thaliana*)(Hirner et al., *Plant J.* 14:535-544, 1998),

```
                                              (SEQ ID NO: 11)
GGTTGCATCT TTGAATACCT TTTTCTCATT TAGGCATAAC

AATATAATAA TTTGTTTTTT GTTTTCATTT TCTTTTGGTG

TCATCTTCAA AAATCTGTAA ACCCAAAAGT TTGTATAACT

TGTTTATTAA GATATTTTTA ATTAAATTTT TTTTTTTGAC

ATTTTTAAAA AATTATAAAG TGTTTTATGA ATTTAAGGAG

TAAATAATAT TTATTTAGAA CACTATAAAT TAGTTTTACA

AGTTCTTAGA AATGTATCTG TAAATTTCAA AAAGGAAAAA

TATAGCATTT AATTTTGAAG ATTTTTTTCT ACATTATATA

TATGATAAAA ATATTGTATT TTGTACTTTG TAGTTACAAA

AAGTCATTAT ATCAACAAAT CTAAATATAA AATATTTTTC

TATATATTAC TCCAAATTAA CTGTCAGAAT AAAAAAGAAG

AATAATTATT ACAGAATCTG AACATTAAAA TCGTCCCTCC

ATATGTGGTC TCTGTCTAGT CCAAAAGCAA TTTACACATC

CCAAGCCGAA ACTATATTAA ATAAACATTT TTTTTTCTTT

AACTAAAACA TTTATAACAT TTAACAATAA AAGTTAAAAA

TCGAACACGT ATAACGTATT TTTTTACGTA TACGTCTTGT

TGGCATATAT GCTTAAAAAC TTCATTACAT ACATATACAA

GTATGTCTAT ATATATGATA TTATGCAAAC ACAAATCTGT

TGACTATAAT TAGACTTCTT CATTTACTCT CTCTCTGACT

TAAAACATTT ATTTTATCTT CTTCTTGTTC TCTCTTTCTC

TTTCTCTCA;
```

LFAH12 (oleate 12-hydroxylase:desaturase gene from *Lesquerella fendleri*)(Broun et al., *Plant J.* 13:201-210, 1998),

```
                                              (SEQ ID NO:12)
TCAGGAAGAT TAAGTCTTTG CTTGTTGTCT GATTTTCTTT

AAATACATTA AGAAATCGGT TATGAAGCTT CGTTTTTTGT

GTTTTGGGAT TATGAAGCTG TCTTTGGATA TTAGTTGCGG

TTATTAGCAT GCTTCTCTTT TGTGTTTTGG GGATGATGAA

GCAGGGTCTC TCTATGTAAT GCATTTTGTT TGAAAACTCA

GCTAATGCTA ATGCAATTTC TTTTGAAACC TTTGTTATGT

TTTCAAAAAT ATTGAATAGG TTCTGTTATG GATTTATTTG

CAAAAGCCAT TGATTAAATC AAACCATTAC ATAAGAACAA

CATTCATTAT TAACTAATTA GAGATGCAAA ACACAACATT

ACATACAACA TCAGTGACTA ATTATTGAGA CAAAACAACA

TCACAGACAC AAACATTCAT CTCATACATC ACTTAGAGAG

ACACAAAAAG CAACCAAACA CAACTATTCC GCCAACAACA

ATTAGCTTCA TACGTTTTGC TTCTCCTTTC AAGCCTTCAA

TCATCTTCTC ACAGCCACGA ATCTGAGCCT TCAATAATAA

CATTTCTTCA TCGTGACACT TCTCACGGTT ATGAATGCAA

GCCTTTATGT CCTCTACTTC TTCTACTAAA GACACATCGG

TCCACTTCCA GGTGTGGAAT CCTCCTCTTT TGAAATTTTT

CTCACAGGTA TGGAATAATC TACCTGGGTT TTTTGGAGTT

CTTGAGGTTC TGATCACAAC ACGGCATCCA CATCGACAGG

TCTTAGGAAA ACCACGAAGG TTATGATCTT CAAGCTCACT

GTCAAAGAT AAAAACGAGT TTGAAGAAGA AGAAGGCATT

ATCAATTTCA GAGAATTTTG GAGAATTTTG AGAGATTGAG
```

-continued

```
AATTGGGAAA TAAGAACCCT AATCCCCAAT TTATGAGATT

GAAAATATAT CCGTTAGAGA AGAAACATAA TGTTGTGCGT

TTTAATTAGA AAAAATAGAG ATGGGCTTTA TCTTTTGTTA

AGAGTTTTGG GCTTGGGCTT GGGTTTTTGA TAAAAAAATT

AATTAAACCA AAACGACGTC GTTTGGTTTA ATTGTTGTTA

AAAAAAAATT AAAACACCAA AACGACGTCG TTTTGGTGTT

ATTAACGGCC TTAAAACGGA TTAAATCCAT AATCCGTCAG

TCAACTAGGG TTACGGATGG TCAACGGCGT TTTTGCATAA

CGGAGGCACA GTTCAGGCTT AACGGAGTGG ACGGAATGGC

TTTTTAGGAA GTTTGTAACC GGGGTCTTTT GTTTATGATG

TATTTGTCCC CGTCGGCTAT TGTTCAGGCC GTTTAGGCCT

TTTTCCTATA TACTGGAAAT AACTATTGTC CAGACGAGTT

ACTTCTCCAA CATATCAAGA AGTGTTACAA AGATGTGTTA

CGAAGCCATA AAACTCAAAA CCCTAAGCCT AAACCCTAGA

ACTTTCTAGC ACGTTTATAC CTTCTCCTTT CTTTAGTTTC

CTTTAAAGGC CTTCGTATCA TAAGTTTTAT TTTTGCTTAA

TACTAACACT AGAAAAAAAC AATAATCAAC ATAAACTAGG

TTAAGTCGTG GATCTAATTT TATTGTGAAA ATGTAATTGC

TTCTCTTAAG AAAAGATTCA TAGCAAAATA TTCGCATCTT

TCTTGTGAAT CATCTTTTGT TTTTGGGGCT ATTAAAGAAA

AATTGAACTC ATGAAATGGT GACAACTTTA TTCTAGAGGT

AACAGAACAA AAATATAGGA ACAACACGTG TTGTTCATAA

ACTACACGTA TAATACTCAA GAAGATGAAT CTTTATAAGA

ATTTAGTTTT CTCATGAAAA CATAAAAAGT TTTGTCAATT

GAAAGTGACA GTTGAAGCAA AGGAACAAAA GGATGGTTGG

TGATGATGCT GAAATGAAAA TGTGTCATTC ATCAAATACT

AAATACTACA TTACTTGTCA CTGCCTACTT CTCCTCTTTC

CTCCGCCACC CATTTTGGAC CCACGAGCCT TCCATTTAAA

CCCTCTCTCG TGCTATTCAC CAGAATAGAA GCCAAGAGAG

AGAGAGAGAT TGTGCTGAGG ATCATTGTCT TCTTCATCGT

TATTAACGTA AGTTTTTTTT TGACCACTTA TATCTAAAAT

CTAGTACATG CAATAGATTA ATGACTGTTC CTTCTTTTGA

TATTTTCAGC;
```

2S2 (2S2 albumin gene from *Arabidopsis thaliana*)(Guerche et al., *Plant Cell* 2:469-478, 1990), FAE1 (fatty acid elongase gene from *Arabidopsis thaliana*)(Rossak et al., *Plant Mol. Biol.* 46:717-725, 2001), and LEC2 (leafy cotyledon gene from *Arabidopsis thaliana*) (Kroj et al., *Development* 130:6065-6073, 2003).

(SEQ ID NO:13)
```
CTTTGTTTTG TAGAGTGTTC TATGGGTTAT GATTTCGAAA

AGAAAAAAAA TTGTGAGACA CTTAATAAAA TTATTTCGAC

AAAAAAAGTA GCTTGTATAA AAAAATCAGA TTTTAATTTA

TGTAAGAACA AATTCCAATA TCCAATAGTT AAAAATAATT

ATTTGTTCCG ATTAATCGAG TTTTGCAAAA TATGCACAAA

ATCTATCAT GTACCATTTC TAAGACTATA TATTTGGTTA

TATATTTTAT GCCGTGTGTT CTGATTCCAA TAAATTTTAG

CGCATAGTAA ATTTTCTAAA AAGCAAAATT TTCTCAAAAG

TGTACTAATG ACAATTAATT GAGTTTCTAC AAAATAAGAA

TAACTATTGA CTCGATTTTC ACAAAACTAG TATGCTAAAT

ATCACATTAC TTTTAAAATT AAATGGAATT ATCTTTTTCA

ATATTGGATA CGAATAATTT TTACACTAAA GTTATTTTAA

TAAAATAACC GTTTATTCAA AATATGTAAA GACGACAAAA

ATATATATTA AATGGAAAAA CGACTAACTT AGTTTTTGCA

AAATTAAATG GATTTGTCCT TTTCAATGTT TGAATACAAA

AAAAAATCTA TAATAAGTTT ATTATATTAA AATAACCCGT

TTTTTCAGAA TACGCAAAAA CGACAAAAAA ATATTAATTA

CAAAGAAATT TAGTTTATA CAAAAATATG AATGGCTATT

AATGGTGTTT ACTCTAAATT TAATTATTAT GCATTTATGC

TAAATCTTTC TAAAGGTACA AAGATTCGTT TTTTCAATG

TTTGAACTGC ATATTAAGGT ATAGATTTGG ACCTTAACAG

AGTTAATATA TAAGGAAGAG AGCCAAGGAA CTCCAAAATA

AAATAAAGAG CCTTCTCTCT CTCTCTCTGA GAAAAAACAC

ATATAGCCAA TGACCTTCTC GTGGTCTTCT GTGCCATAAA

AGCCATTATA TACATTCAAA CACAATCTGG CGCCACATAT

ACACATGTAC TAGTGTATGT ATATGTCCTA ACCTCTGTAT

TCATATCTCT CTCCTTGTCT GAGTGGTGCG ATGGGTATCC

CCATAAGCTG CAAACATTGA ACCATCTGCA ACATTTTGAC

TCGTTTTCTT TTGTGTTTTT CCAACATCTG TCTCTTCTTC

ACTCGCTCTC TCCTAATCAA TCTCCCCAAC GACCTCTCTT

TTTTTTTGTT TCTTCACTCA GATCTCTCTC CCTCTCTCTC

TCTCTCTCTC CGGGAAAA
```

All five promoters give early embryo expression in *Arabidopsis*. The expression profiles of the five promoters during early embryo development are represented schematically in FIG. 1. The AAP1, LFAH12, 2S2, and FAE1 promoters are off in the earliest stage of embryo development. They become transcriptionally active at progressively later stages in development starting with AAP1 followed by LFAH12, 2S2, and then FAE1. All four promoters then remain active through later embryonic development stages. The LEC2 promoter has an inverse expression profile, is active in very early embryo development and then declines in activity gradually through later stages.

The AAP1, LFAH12, 2S2, FAE1, and LEC2 promoters were combined with either of two configurations of the REV coding region sequence in the REV transgene expression constructs. The AAP1, LFAH12, 2S2, FAE1, and LEC2 promoters were combined with the REV gene coding sequence including all introns as present in the REV gene. The AAP1 and LFAH12 promoters were also combined with a REV coding region sequence derived from a REV cDNA lacking introns.

*Arabidopsis thaliana* REV (AtRev) cDNA

```
                                          (SEQ ID NO:1)
ATGGAGATGG CGGTGGCTAA CCACCGTGAG AGAAGCAGTG

ACAGTATGAA TAGACATTTA GATAGTAGCG GTAAGTACGT

TAGGTACACA GCTGAGCAAG TCGAGGCTCT TGAGCGTGTC

TACGCTGAGT GTCCTAAGCC TAGCTCTCTC CGTCGACAAC

AATTGATCCG TGAATGTTCC ATTTTGGCCA ATATTGAGCC

TAAGCAGATC AAAGTCTGGT TTCAGAACCG CAGGTGTCGA

GATAAGCAGA GGAAAGAGGC GTCGAGGCTC CAGAGCGTAA

ACCGGAAGCT CTCTGCGATG AATAAACTGT TGATGGAGGA

GAATGATAGG TTGCAGAAGC AGGTTTCTCA GCTTGTCTGC

GAAAATGGAT ATATGAAACA GCAGCTAACT ACTGTTGTTA

ACGATCCAAG CTGTGAATCT GTGGTCACAA CTCCTCAGCA

TTCGCTTAGA GATGCGAATA GTCCTGCTGG ATTGCTCTCA

ATCGCAGAGG AGACTTTGGC AGAGTTCCTA TCCAAGGCTA

CAGGAACTGC TGTTGATTG GGTTCAGATG CCTGGGATGA

AGCCTGGTCC GGATTCGGTT GGCATCTTTG CCATTTCGCA

AAGATGCAAT GGAGTGGCAG CTCGAGCCTG TGGTCTTGTT

AGCTTAGAAC CTATGAAGAT TGCAGAGATC CTCAAAGATC

GGCCATCTTG GTTCCGTGAC TGTAGGAGCC TTGAAGTTTT

CACTATGTTC CCGGCTGGTA ATGGTGGCAC AATCGAGCTT

GTTTATATGC AGACGTATGC ACCAACGACT CTGGCTCCTG

CCCGCGATTT CTGGACCCTG AGATACACAA CGAGCCTCGA

CAATGGGAGT TTTGTGGTTT GTGAGAGGTC GCTATCTGGC

TCTGGAGCTG GGCCTAATGC TGCTTCAGCT TCTCAGTTTG

TGAGAGCAGA AATGCTTTCT AGTGGGTATT TAATAAGGCC

TTGTGATGGT GGTGGTTCTA TTATTCACAT TGTCGATCAC

CTTAATCTTG AGGCTTGGAG TGTTCCGGAT GTGCTTCGAC

CCCTTTATGA GTCATCCAAA GTCGTTGCAC AAAAAATGAC

CATTTCCGCG TTGCGGTATA TCAGGCAATT AGCCCAAGAG

TCTAATGGTG AAGTAGTGTA TGGATTAGGA AGGCAGCCTG

CTGTTCTTAG AACCTTTAGC CAAAGATTAA GCAGGGGCTT

CAATGATGCG GTTAATGGGT TTGGTGACGA CGGGTGGTCT

ACGATGCATT GTGATGGAGC GGAAGATATT ATCGTTGCTA

TTAACTCTAC AAAGCATTTG AATAATATTT CTAATTCTCT

TTCGTTCCTT GGAGGCGTGC TCTGTGCCAA GGCTTCAATG

CTTCTCCAAA ATGTTCCTCC TGCGGTTTTG ATCCGGTTCC

TTAGAGAGCA TCGATCTGAG TGGGCTGATT TCAATGTTGA
```

-continued
```
TGCATATTCC GCTGCTACAC TTAAAGCTGG TAGCTTTGCT

TATCCGGGAA TGAGACCAAC AAGATTCACT GGGAGTCAGA

TCATAATGCC ACTAGGACAT ACAATTGAAC ACGAAGAAAT

GCTAGAAGTT GTTAGACTGG AAGGTCATTC TCTTGCTCAA

GAAGATGCAT TTATGTCACG GGATGTCCAT CTCCTTCAGA

TTTGTACCGG GATTGACGAG AATGCCGTTG GAGCTTGTTC

TGAACTGATA TTTGCTCCGA TTAATGAGAT GTTCCCGGAT

GATGCTCCAC TTGTTCCCTC TGGATTCCGA GTCATACCCG

TTGATGCTAA AACGGGAGAT GTACAAGATC TGTTAACCGC

TAATCACCGT ACACTAGACT TAACTTCTAG CCTTGAAGTCG

GTCCATCACC TGAGAATGCT TCTGGAAACT CTTTTTCTAG

CTCAAGCTCG AGATGTATTC TCACTATCGC GTTTCAATTC

CCTTTTGAAA ACAACTTGCA AGAAAATGTT GCTGGTATGG

CTTGTCAGTA TGTGAGGAGC GTGATCTCAT CAGTTCAACG

TGTTGCAATG GCGATCTCAC CGTCTGGGAT AAGCCCGAGT

CTGGGCTCCA AATTGTCCCC AGGATCTCCT GAAGCTGTTA

CTCTTGCTCA GTGGATCTCT CAAAGTTAC AGTCATCACT

TAGGCTCGGA GTTGCTGACG ATTGATTCAC TTGGAAGCGA

CGACTCGGTA CTAAAACTTC TATGGGATCA CCAAGATGCC

ATCCTGTGTT GCTCATTAAA GCCACAGCCA GTGTTCATGT

TTGCGAACCA AGCTGGTCTA GACATGCTAG AGACAACACT

TGTAGCCTTA CAAGATATAA CACTCGAAAA GATATTCGAT

GAATCGGGTC GTAAGGCTAT CTGTTCGGAC TTCGCCAAGC

TAATGCAACA GGGATTTGCT TGCTTGCCTT CAGGAATCTG

TGTGTCAACG ATGGGAAGAC ATGTGAGTTA TGAACAAGCT

GTTGCTTGGA AAGTGTTTGC TGCATCTGAA GAAAACAAC

AACAATCTGC ATTGTCTTGC CTTCTCCTTT GTAAACTGGT

CTTTTGTGTG A.
```

REV Transgene Constructs
LFAH12-At REV Gene-rev 3' UTR

A 2170 base pair (bp) region of the LFAH12 promoter was amplified from *Lesquerella fendleri* genomic DNA with EcoRI-LFAH12 (GAATTCTCAGGAAGAT-TAAGTCTTTGCTTG; SEQ ID NO: 14) and SacI-LFAH12 (GAGCTCGCTGAAAATATCAAAAGAAGGAACA; SEQ ID NO: 15) primers. These primers started 24 nucleotides and 15 nucleotides in from the 5' and 3' ends, respectively, of the published LFAH12 sequence ((GenBank® designations AF016103.1 or GI:3452128) (Broun et al., *Plant J.* 13:201-210 (1998)). Several independent PCR reactions were cloned into pCR-Blunt (Invitrogen) and sequenced. The sequences of all were identical to one another (SEQ ID NO:12) and 97% identical to the published LFAH12 sequence. The differences could be due to the specific accession of *L. fendleri* used for the retrieval of the promoter. LFAH12 was moved to the pBluescript plasmid with EcoRI and the orientation of the promoter in pBluescript was determined to be KpnI on the 5' side of the promoter and SpeI on the 3' side of the promoter (pTG143). The At REV gene-rev 3' UTR cassette was taken as a SpeI-KpnI fragment from pTG95 (35S-At REV gene-rev 3'UTR in pCGN1547, patent WO 01/33944A1) and along with the LFAH12 promoter (KpnI-SpeI fragment from pTG143), was ligated into pCGN1547 binary vector (McBride et al., *Plant Mol. Biol.* 14:269-276, 1990) that had been cut with KpnI in a three-way ligation to create LFAH12 promoter-At REV gene-rev 3' UTR in a tail-to-tail orientation with the plant NPTII expression cassette.

AAP1-At REV Gene-rev 3' UTR

An 809 base pair (bp) region of the AAP1 promoter was amplified from *Arabidopsis thaliana* (ecotype Columbia) genomic DNA with EcoRI-AAP1 (GAATTCGGTTG-CATCTTTGAATACCTTTTT; SEQ ID NO:16) and SacI-AAP1 (GAGCTCTGAGAGAAAGAGAAAGAGAGAA-CAA; SEQ ID NO:17) primers. The SacI-AAP 1 primer started 6 nucleotides in from the 3' end of the published AAP1 sequence (GenBank® deposit designation X95622.1; GI:1566687) (Himer et al., *Plant J.* 14:535-544, 1998). The sequences of all PCR products were identical to one another, 98% identical to the published C24 ecotype AAP1 sequence, and 100% identical to the annotated Col ecotype AAP1 sequence (GenBank® designation AC008051.3; GI:7462019) (SEQ ID NO:11). AAP1 was moved to the plasmid pBluescript with EcoRI and the orientation of the promoter in pBluescript was determined to be KpnI on the 5' side of the promoter and SpeI on the 3' side of the promoter (pTG145). The At REV gene-rev 3' UTR cassette was taken as a SpeI-KpnI fragment from pTG95 (35S-At REV gene-rev 3'UTR in pCGN1547, See WO 01/33944A1) and along with the AAP1 promoter (KpnI-SpeI fragment from pTG145), was ligated into pCGN1547 binary vector (McBride et al., *Plant Mol. Biol.* 14:269-276, 1990) that had been cut with KpnI in a three-way ligation to create AAP1 promoter-At REV gene-rev 3' UTR in a head-to-tail orientation with the plant NPTII expression cassette.

LFAH12-At REV cDNA-rev 3' UTR

At REV cDNA was amplified from cDNA synthesized from total RNA isolated from *Arabidopsis* leaf of the Columbia ecotype. The primers used incorporated an NcoI site at the ATG and a BamHI site after the stop codon: NcoI-ATG rev CCATGGAGATGGCGGTGGC TAAC (SEQ ID NO:18) and BamHI-TGA rev GGATCCTCACACAAAAGACCAGTT-TAC AAAGGA (SEQ ID NO: 19). The resulting At REV cDNA PCR product was cloned into the plasmid pCR-Blunt and sequenced (pTG230). Using pTG95 as the template, Rev 3' UTR was amplified with primers that incorporated an EcoRV site at the 5' end and NotI/KpnI at the 3' end: EcoRV revUTR GATATCTTCGATTGACAGAAAAAG (SEQ ID NO:20) and Not/Kpn revUTR GCGGCCGCGGTACCCT-CAACCAACCACATGGAACCA (SEQ ID NO:21). The resulting At REV 3'UTR was cloned into the plasmid pCR-Blunt and sequenced. Rev 3' UTR was moved to the plasmid pBluescript with EcoRV and NotI sites (pTG234). Rev 3' UTR was then taken from pTG234 and ligated into pTG230 with EcoRV and NotI sites (pTG239). The At REV cDNA-rev 3'UTR cassette was taken as a SpeI-KpnI fragment from pTG239 and along with the LFAH12 promoter (KpnI-SpeI fragment from pTG143), was ligated into the pCGN1547 binary vector in a three-way ligation to create LFAH12-At REV cDNA-rev 3'UTR in a head-to-tail orientation with the plant NPTII expression cassette (pTG241).

AAP1-At REV cDNA-rev 3'UTR

The At REV cDNA-rev 3'UTR cassette was taken as a SpeI-Kpn fragment from pTG239 and along with the AAP1 promoter (KpnI-SpeI fragment from pTG145), was ligated into the pCGN1547 binary vector in a three-way ligation to create AAP1-At REV cDNA-rev 3'UTR in a head-to-tail orientation with the plant NPTII expression cassette (pTG242).

FAE1-At REV Gene-rev 3'UTR

The 933 bp FAE1 promoter was amplified from a CD vector with KpnI and SpeI sites, cloned into the plasmid pCR-Blunt, and sequenced (pTG238). FAE1 promoter was then moved into the plasmid pBluescript with EcoRI (pTG243). The At REV gene-rev 3' UTR cassette was taken as a SpeI-KpnI fragment from pTG95 and along with the FAE1 promoter (KpnI-SpeI fragment from pTG243), was ligated into the pCGN1547 binary vector (McBride et al., *Plant Mol. Biol.* 14:269-276, 1990) that had been cut with KpnI in a three-way ligation to create FAE1 promoter-At REV gene-rev 3'UTR in a head-to-tail orientation with the plant NPTII expression cassette (pTG248).

2S2-At REV Gene-rev3'UTR

The 1379 bp 2S2 promoter was excised from CD plasmid p4163 (2S2-At REV SwaI fragment and ligated into pBluescript at the EcoRV site. The orientation of the promoter in pBluescript was determined to be KpnI on the 5' side of the promoter and BamHI on the 3' side of the promoter (pTG251). The At REV gene-rev3'UTR cassette was taken as a BamHI-KpnI fragment from pTG138(35S-At REV gene-rev3'UTR in TOPO) and along with the 2S2 promoter (KpnI-BamHI fragment from pTG251), was ligated into pCGN1547 binary vector (McBride et al., *Plant Mol. Biol.* 14:269-276, 1990) that had been cut with KpnI in a three-way ligation to create 2S2 promoter-At REV gene-rev3'UTR in a head-to-tail orientation with the plant NPTII expression cassette.

LEC2-At REV Gene-rev3'UTR

The 1256 bp LEC2 promoter was excised from CD plasmid p5217 with ApaI and PstI and cloned into the plasmid pBluescript at the same sites (pTG252). The promoter was then taken as a KpnI-BamHI fragment into pTG112 (At REV gene in the plasmid pCR-Blunt) linearized at the same sites to give pTG280, which is the LEC2-At REV gene in the pCR-Blunt plasmid. Using pTG234 as the template, Rev 3'UTR was amplified with primers that incorporated a NotI site at the 5' end and NotI/KpnI at the 3' end: Not REV UTR start GCG-GCCGCTTCGATTGACAGAAAAAG (SEQ ID NO:22) and NotKpn Rev UTR GCGGCCGCGGTACCCTCAAC-CAACCACATGGAACCA (SEQ ID NO:23). The resulting At REV 3'UTR was cloned into the plasmid pCR-Blunt and sequenced (pTG281). The Rev 3'UTR was then moved to pTG280 using the NotI sites and screened for proper orientation. The resulting plasmid was LEC2-At REV gene-rev 3'UTR in the plasmid pCR-Blunt (pTG283). LEC2-At REV gene-rev 3'UTR was moved as a KpnI fragment to a pCGN1547 plasmid linearized with KpnI and screened for head-to-tail orientation with the plant NPTII expression cassette (pTG288).

Canola (*Brassica napus*) Transformation

The double haploid canola variety DH12075 was transformed with the REV transgene expression constructs using an *Agrobacterium*-mediated transformation method based on that of Maloney et al (Maloney et al., *Plant Cell Reports* 8:238, 1989)

Sterilized seeds were germinated on ½ MS (Murashige & Skoog) media with 1% sucrose in 15×60 mm Petri dishes for 5 days with approximately 40 to about 60 seeds per plate. A total of approximately 1500 seeds were germinated for each transformation construct. Seeds were not fully submerged in the germination medium. Germinated seedlings were grown in a tissue culture room at 25° C., on a 16 hour light/8 hour dark cycle.

Cotyledons were cut just above the apical meristem without obtaining any of the meristem tissue. This was done by gently gripping the two petioles with forceps immediately above the apical meristem region. Care was taken not to crush the petioles with the forceps. Using the tips of the forceps as a guide, petioles were cut using a scalpel with a sharp No. 12 blade. Cotyledons were released onto a 15 mm×100 mm plate of co-cultivation medium. Properly cut cotyledons separate easily. If they did not, there was a very good chance that meristematic tissue had been obtained and such cotyledons were not used. Each plate held approximately 20 cotyledons. Cotyledon explants were inoculated with *Agrobacterium* after every few plates that were prepared to avoid wilting which would have a negative impact on following stages of the protocol.

REV transformation constructs were introduced into *Agrobacterium tumefaciens* by electroporation. *Agrobacterium* harboring the REV transformation construct was grown in AB medium with appropriate antibiotics for two days shaking at 28° C. To inoculate cotyledon explants, a small volume of *Agrobacterium* culture was added to a 10 mm×35 mm Petri dish. The petiole of each explant was dipped into the *Agrobacterium* culture and the cut end placed into co-cultivation medium in a Petri dish. The plates were sealed and placed in a tissue culture room at 25° C., 16 hour light/8 hour dark for 3 days.

After 3 days, explants were transferred in sets often to fresh 25 mm×100 mm Petri dishes containing shoot induction medium. This medium contained a selection agent (20 mg/l Kanamycin) and hormone (4.5 mg/l a brassinosteroid (BA)). Only healthy-looking explants were transferred. Explants were kept on shoot induction medium for 14 to 21 days. At this time, green calli and possibly some shoot development and some non-transformed shoots may could be observed. Non-transformed shoots were easily recognized by their white and purple color. Kanamycin-sensitive shoots were removed by cutting them away and all healthy-looking calli were transferred to fresh plates of shoot induction medium. The explants were kept on these plates for another 14 to 21 days.

After 2 to 3 weeks, shoots that were dark green in color were transferred to plates containing shoot elongation medium. This medium contained a selection agent (20 mg/l Kanamycin) but did not contain any hormones. Five shoots were transferred to each plate. The plates were sealed and returned to the tissue culture room. Transformed shoots that appeared vitrious were transferred to shoot elongation medium containing phloroglucinol (150 mg/l). Shoots that became healthy and green were returned to shoot elongation medium plates. Repeated transfers of vitrious shoots to fresh plates of the same medium were required in some cases to obtain normal looking shoots.

Shoots with normal morphology were transferred to 4 oz. baby food jars with rooting medium containing 0.5 mg/l indole butyric acid. Any excess callus was cut away when transferring shoots to the jars. Shoots could be maintained in jars indefinitely by transferring them to fresh jars containing 0.2 mg/l indole butyric acid approximately every 6 weeks.

Once a good root system had formed, the $T_0$ generation shoots were removed from jars, agar removed from the roots, and the plantlet transferred to potting soil. Each independent $T_0$ plantlet represented an independent occurrence of insertion of the transgene into the canola genome and was referred to as an event. A transparent cup was placed over the plantlet for a few days, allowing the plant to acclimatize to the new environment. Once the plant had hardened, the cup was removed. The $T_0$ transgenic events were then grown to maturity in the greenhouse and $T_1$ seeds collected.

$T_0$ Event Characterization

The number of transgene insertion site loci was determined in each event by Southern analysis. REV transgene expression in the $T_0$ events was verified by Northern analysis or end-point RT-PCR. REV expression data were obtained for a single time point in embryo development, 19 days after pollination (DAP). From these data it was concluded that, at this developmental time point, the LFAH12 and 2S2 albumin promoters were driving higher levels of REV RNA production than the AAP1 promoter. The 2S2/REV constructs gave moderate to high level expression in many events. The expression data demonstrated that all five promoters were functional in driving REV transgene expression in transgenic canola plants.

$T_0$ plants were successfully generated for all seven REV transgene constructs. The tested constructs included (a) AAP1/REV gene; (b) AAP1/REVcDNA; (c) LFAH12/REV gene; (d) LFAH12/REVcDNA; (e) 2S2/REV gene; (f) FAE1/REV gene; and (g) LEC2/REV gene.

Example 2

Evaluation of the Effect of REV Transgene Expression During Embryo Development on Canola Yield in Replicated Field Trials In this example the transgenic canola plants comprising the *Arabidopsis* REV transgene under the control of the various embryo specific promoters were tested in field trials.

Advancement of Transgenic REV Events to Field Trials.

$T_0$ events were selected for advancement to field trials based on a combination of transgene expression and transgene insertion locus number. Events with verified transgene expression and a single transgene insertion locus were assigned the highest priority to be carried forward to field testing. In some instances, events with multiple insertion loci were selected if the presence of multiple genes gave a high overall transgene expression level due to gene dosage.

$T_1$ seeds from selected events were grown as segregating $T_1$ populations in field plots. Each event was planted as a two row, twenty four plant plot. For events with a single transgene insertion locus, segregation of the transgene among the twenty four $T_1$ plants would produce a distribution of approximately six null plants lacking the transgene, twelve heterozygous plants, and six homozygous plants. Each $T_1$ plant was individually bagged before flowering to prevent out-crossing. $T_2$ seeds from each of the twenty four $T_1$ plants were harvested separately.

The $T_2$ seed stocks were used to identify which of the twenty four parent $T_1$ plants were null, heterozygous, or homozygous. Approximately thirty $T_2$ seeds from each $T_1$ plant were germinated on filter paper in petri dishes with a solution containing the antibiotic G418, an analog of kanamycin. Since the plants were co-transformed with the nptII resistance gene as a selectable marker, only those seeds carrying the transgene would germinate and continue to grow. If all the seeds on a plate proved to be sensitive to G418, then the $T_1$ parent was identified as a null line. If all the seeds on a plate were resistant to G418, then the $T_1$ parent was identified as a homozygous line. If approximately one quarter of the seeds on a plate were sensitive and the rest resistant, the $T_1$ parent was identified as a heterozygous line. $T_2$ seeds from homozygous $T_1$ parents from the same transformation event were bulked to generate homozygous seed stocks for field trial testing. $T_2$ seeds from null $T_1$ parents from the same transformation event were bulked to generate null sibling seed stocks for field trial testing.

Field Trial Design

The use of embryo-specific promoters to evaluate the potential of the REV transgene as a yield enhancing gene was tested in the transgenic canola lines by comparing each transgenic line directly with its null sibling in the field in large scale replicated trials. Since the null sibling arises from segregation of the transgene in the $T_1$ generation, the null and homozygous siblings are nearly identical genetically. The only significant difference is the presence or absence of the REV transgene. This near genetic identity makes the null sibling the optimal control for evaluation of the effect of the REV transgene. As the main objective of the trial was the comparison of the transgenic line from an event to its null segregant, a split plot design was chosen. This design gives a high level of evaluation to the interaction between the transgenic and non-transgenic subentries and the differences between transgenic subplots between events (the interaction of subplot and main plot) and a lower level of evaluation to the differences between overall events or the main plot.

Field trials were conducted at multiple locations across prairie environments to assess yield phenotypes under the range of environmental conditions in which canola is typically grown. At all locations, each transgenic event was physically paired with its null sibling in adjacent plots. Each plot pair of homozygous and null siblings was replicated four times at each trial location. The locations of the four replicate plot pairs in each trial were randomly distributed at each trial location. Plots were 1.6 m by 6 m and planted at a density of approximately 142 seeds per square meter. Plants were grown to maturity using standard agronomic practices typical to commercial production of canola.

Example 3

Expression of a REV Transgene from an Embryo-specific Promoter to Increase Seed Yield in Transgenic Canola All plots at each yield field trial location were individually harvested with a combine. Total seed yield data were collected as total seed weight adjusted for moisture content from each plot. For every transgenic event in each trial, the mean of the total yield from the four replicate plots of each homozygous line was compared to the mean of the total yield from the four replicate plots of the associated null sibling line. This comparison was used to evaluate the effect of the REV transgene on total seed yield. Results from each of the multiple trial locations were combined to give an across trials analysis of the effect of the REV transgene on total seed yield. Statistical analysis of variance at each trial location permitted the assignment of a threshold for significance (P=0.05) for differences in total seed yield between homozygous transgenic lines and their null siblings.

The transgenic REV canola lines that showed a statistically significant increase in total seed yield are summarized in Table 1. Transgenic lines showing statistically significant increases in total yield were identified for all seven promoter/REV transgene constructs. These results demonstrate that over expression of REV using an embryo-specific promoter results in increased seed yield. The greatest impact on yield was obtained with the LEC2 promoter suggesting that over expression of REV may be most effective in the earliest stage of embryo development since the LEC2 promoter is maximally active very early in development with decreasing transcriptional activity through the later stages of embryo development. The AAP1, LFAH12, and 2S2 promoters initiate transcriptional activity at progressively later stages in embryo development but were also effective in increasing yield. The LFAH12 promoter was notable for the number of independent events that were recovered that showed significantly increased yield indicating a high degree of penetrance for the trait using this promoter. Only one event with a moderate increase in yield was recovered for the FAE1 promoter possibly suggesting that promoters that initiate transcriptional activity in earlier stages of embryo development provide the best means for yield increase and demonstrate that early embryonic overexpression of a gene can be used to evaluate whether a gene involved in plant growth and/or development has potential to increase crop yield in transgenic plants.

TABLE 1

Change in total seed yield in homozygous REV plants relative to their null siblings.

| Event | Promoter | Transgene | % Yield Increase |
|---|---|---|---|
| TG6-21 | AAP1 | REV gene | 7.8 |
| TG12-6 | AAP1 | REV cDNA | 7.9 |
| TG5-32 | LFAH12 | REV gene | 15.5 |
| TG11-4 | LFAH12 | REV cDNA | 18.9 |
| TG11-13 | LFAH12 | REV cDNA | 8.9 |
| TG11-17 | LFAH12 | REV cDNA | 16.7 |
| TG11-18 | LFAH12 | REV cDNA | 5.8 |
| TG11-23 | LFAH12 | REV cDNA | 9.4 |
| TG20-5 | 2S2 | REV gene | 25.6 |
| TG10-16 | FAE1 | REV gene | 5.6 |
| TG19-8 | LEC2 | REV gene | 59.8 |

All values are statistically significant (P = 0.05).

Example 4

Increased Seed Size in Transgenic Canola Expressing Rev During Embryo Development Using Embryo-Specific Promoters All seeds harvested from individual plots in the field trials were dried at low heat in an oven to uniform moisture content. For each seed sample for each plot in the field trials, one thousand seeds were counted out using an Agriculex (Guelph, Ontario, Canada) seed counter. The weight of each one thousand seed sample was then measured. The mean of the thousand seed weight (TSW) from the four replicate plots of each homozygous line was compared to the mean of TSW from the four replicate plots of the associated null sibling line. The differences in TSW values between homozygous transgenic REV lines and their null sibling lines were used as a measure of differences in seed size that could be attributed to the REV transgene. Statistical analysis of variance at each trial location permitted the assignment of a threshold for significance (P=0.05) for differences in TSW between homozygous transgenic lines and their null siblings.

The transgenic REV canola lines that showed a statistically significant increase in seed size as indicated by TSW are summarized in Table 2. Transgenic lines showing statistically significant increases in TSW were identified for six of the seven promoter/REV transgene constructs. Effects of the LEC2 and LFAH12 promoters driving REV expression on seed size were consistent with effects observed on total yield using these promoters. The LEC2/REV construct gave a strong positive increase in seed size indicating that over expression of REV in very early embryo development is effective. The LFAH12 promoter again showed a strong penetrance of the trait with six independent events showing statistically significant increases in seed size. The AAP1 and 2S2 promoters driving REV over expression also gave statistically significant increases in seed size. No events carrying the FAE1/REV transgene construct showed a significant increase in TSW. Since the activity of the FAE1 promoter initiates the latest in embryo development of the five promoters tested, the lack of an effect suggests that promoters that initiate transcriptional activity in the earlier stages of embryo development provide a means to increase yield when associated with a gene that affects plant growth and development, such as REV. In addition, these promoters can be used to evaluate other plant genes associated with growth and/or development for their potential to increase yield, such as seed size and/or number, in transgenic plants.

TABLE 2

Change in seed size as indicated by 1000 seed weight.

| Event | Promoter | Transgene | % 1000 Seed Weight Increase |
|---|---|---|---|
| TG6-21-15 | AAP1 | REV gene | 3.9 |
| TG12-6-6 | AAP1 | REV cDNA | 3.6* |
| TG5-32-23 | LFAH12 | REV gene | 5.8 |
| TG5-61 | LFAH12 | REV gene | 4.8 |
| TG11-4 | LFAH12 | REV cDNA | 7.9 |
| TG11-13-9 | LFAH12 | REV cDNA | 4.8 |
| TG11-17-19 | LFAH12 | REV cDNA | 3.1 |
| TG11-18-19 | LFAH12 | REV cDNA | 4.8 |
| TG20-15 | 2S2 | REV gene | 2.7 |
| TG19-8 | LEC2 | REV gene | 3.1 |
| TG19-23 | LEC2 | REV gene | 7.7 |

All values are statistically significant (P = 0.05). Value indicated by an * was significant at one trial location.

Example 5

Increased Seed Size and Yield in Transgenic Canola Expressing Rev During Embryo Development Using Embryo-Specific Promoters One conceivable outcome for an increased seed size phenotype can be a compensating response by the plant that results in decreased seed number to maintain a constant net allocation of resources to seed production. Table 3 summarizes six independent transgenic REV events that demonstrated both a statistically significant increased seed size and an increase in total yield in field trials. Simultaneous increases in seed size and total yield were observed in events carrying AAP1/REV, LFAH12/REV, 2S2/REV, and LEC2/REV transgene constructs indicating that all four promoters were effective in increasing seed size without eliciting a reduction in seed number as a compensating response by the plant.

Comparison of TSW values with total yield values in Table 3 revealed that the increased seed size did not account for the observed total increases in yield. Increased seed size was one component contributing to total yield. The remainder of the increased yield was due to increased seed number. In most cases, increased seed number was the major component of increased total yield. Increased seed number could result from an increase in seed number per pod, an increase in the number of racemes, an increase in the number of pods per raceme, a decrease in seed abortion rate, or a combination of these effects.

The absence of events carrying the FAE1/REV transgene construct from the list of events showing both increase seed size and total yield indicates that promoters that initiate transcriptional activity in the earlier stages of embryo development provide the best means for evaluating plant genes involved in plant development and growth for their potential to increase seed size and yield in transgenic plants. It also appears that the greatest efficacy for yield increase may be obtained with promoters that initiate transcriptional activity in the earlier stages of embryo development.

TABLE 3

Independent transgenic REV events showing both increased seed size and total yield.

| Event | Promoter | Transgene | % 1000 Seed Weight Increase | % Yield Increase |
|---|---|---|---|---|
| TG6-21 | AAP1 | REV gene | 3.9 | 7.8 |
| TG12-6-6 | AAP1 | REV cDNA | 16.2* | 103.9* |
| TG5-32-14 | LFAH12 | REV gene | 5.3 | 5.7 |
| TG11-4 | LFAH12 | REV cDNA | 7.9 | 18.9 |
| TG20-15 | 2S2 | REV gene | 2.7 | 8.6** |
| TG19-8 | LEC2 | REV gene | 3.1 | 59.8 |

Values are statistically significant (P = 0.05) except ** which was not statistically significant but positive at all four trial locations. Values marked with * were significant at one trial location.

Example 6

Transgenic Soybean Plants Expressing Transgene Constructs Designed to Confer Embryo-Specific Expression of REVOLUTA Based on the successful use of the LFAH12 embryo-specific promoter to drive REVOLUTA transgene expression in transgenic canola plants (Tables 1, 2, and 3) to obtain yield and seed size increase, an LFAH12-AtREV gene construct was built for transformation of soybean. Soybean, like canola, is a dicot and the high conservation of REVOLUTA genes across plant species made it likely that the *Arabidopsis* REVOLUTA gene would function when introduced into transgenic soybean plants.

REV Transgene Construct
LFAH12-AtREV Gene-rev 3' UTR

A 2170 bp region of the LFAH12 promoter was amplified from *Lesquerella fendleri* genomic DNA with EcoRI-LFAH12 (GAATTCTCAGGAAGATTAAGTCTTTGC TTG; SEQ ID NO: 14) and SacI-LFAH12 (GAGCTCGCT-GAAAATATCAAAAGAAGGAACA; SEQ ID NO: 15) primers. These primers started 24 nucleotides and 15 nucleotides in from the 5' and 3' ends, respectively, of the published LFAH12 sequence ((GenBank® designations AF016103.1 or GI:3452128) (Broun et al., *Plant J.* 13:201-210 (1998)). Several independent PCR reactions were cloned into pCR-Blunt (Invitrogen) and sequenced. The sequences of all were identical to one another and 97% identical to the published LFAH12 sequence. The differences could be due to the specific accession of *L. fendleri* used for the retrieval of the promoter. LFAH12 was moved to the pBluescript II plasmid with EcoRI and the orientation of the promoter in pBluescript was determined to be KpnI on the 5' side of the promoter and SpeI on the 3' side of the promoter (pTG143). The At REV gene-rev 3' UTR cassette was taken as a SpeI-KpnI fragment from pTG95 (35S-At REV gene-rev 3'UTR in pCGN1547, patent WO 01/33944A1) and along with the LFAH12 promoter (KpnI-SpeI fragment from pTG143), was ligated into pCGN1547 binary vector (McBride et al., *Plant Mol. Biol.* 14:269-276, 1990) that had been cut with KpnI in a three-way ligation to create LFAH12 promoter-At REV gene-rev 3' UTR in a head-to-tail orientation with the plant NPTII expression cassette (pTG171). The LFAH12pr-At REV gene-rev 3'

UTR cassette was excised from pTG171 with KpnI, blunted with T4 polymerase and cloned into pBluescript II that had been cut with SmaI to give pTG464 (TG-GM6).

Soybean Transformation

The soybean variety X5 was transformed with the REV transgene expression construct using the biolistic method to introduce DNA on gold particles into soybean cells grown in suspension culture. Linear DNA containing the REV transgene expression construct was co-transformed with a hygromycin selectable marker gene on a separate linear DNA fragment.

To prepare DNA for insertion into soybean cells, 2.5 µl REVDNA and 2.5 µl pHYGR$^R$ DNA were added to gold particles. 50 µl CaCl$_2$ was added and vortexed 5 sec. Followed by addition of 20 µl spermidine and vortexed 5 sec. Precipitate was allowed to settle to the bottom of the tube. The supernatant was removed and the pellet washed twice with 200 µl 100% ethanol. The supernatant was removed and the pellet resuspended in 120 µl 100% ethanol. 8 µl was aliquoted per disk for insertion.

After biolistics insertion, cells were grown in suspension culture in flasks for 12 days. Cultures were then transferred to new flasks containing 30 ml of 2.4% Sugar+Finer's Light (F.L.)+170 µl of 10 µg/µl Hygromycin (hyg). For the following four weeks, media was changed weekly by transferring to a new flask with 2.4% Sugar+F.L.+hyg.

Transformed green calli developed in the flasks during the fifth through tenth weeks. The contents of flasks with green calli were poured into sterile 100×15 mm dishes or lids. Using sterile forceps, green calli were teased from brown cells and transferred to 26-well plates filled with 1-2 ml 2.4% Sugar+F.L.+Hyg/well. 1 green callus (clone)/well. The goal was to get 20-30 clones/flask.

Media was changed in the plates every 2 weeks using a sterile 10-mL pipette and automatic pipetor to suck all media from all wells. Medium was replaced with fresh 2.4% Sugar+Hyg. Plates were monitored for suitable proembryogenic cultures. These were green with several proembryogenic projections and showed rapid division and growth. Once a suitable cell mass was identified by microscopic observation, it was transferred onto a sterile dish or lid where as much dead cell matter as possible was removed. The remaining piece of tissue was transferred to a regular 30 ml flask of 2.4% Sugar+Hyg. Clones were allowed to grow about 3 to 5 weeks between media changes.

When clones were grown sufficiently, they were split. Only the 5 best pieces per clone were kept. These were green with several proembryogenic projections. Smooth, green colonies were not desired. The clones were subcultured every 3-5 weeks until they were sufficiently large. At this point, clones were transferred to a soy bean regeneration medium with activated charcoal to remove 2,4D (OMSM6AC; Simmonds and Donaldson, Plant Cell Reports 19:485-490, 2000, incorporated herein by reference in its entirety) as the first step of regeneration.

Clones were grown no more than six days on OMSM6AC containing activated charcoal (AC) to remove 2,4-D from tissue. Clones were then transferred to soybean germination medium (OMSM6G, Simmonds and Donaldson, supra) for three weeks. This medium allows for the development of embryos. After three weeks, the best 20 embryos were chosen and transferred to a soybean maturation medium (OMSM6PH, Simmonds and Donaldson, supra). The best embryos were single (as opposed to fused) embryos with 1 or 2 cotyledons and a visible meristem. Embryos were transferred so that the meristem was parallel to agar surface. Clones were maintained on OMSM6PH for four weeks during which time embryos turned a yellow color. Once yellow, they were ready to be desiccated and regenerated to plants.

Embryos were desiccated in Magenta boxes sterilized 30 min with 3 layers of H$_2$O-saturated Whatman filters at bottom. Embryos were desiccated ten days and then transferred to a soybean rooting medium (B5/2 medium, Simmonds and Donaldson, supra) in plates for about 10 to 12 days. Plantlets were ready to go to Sunshine Mix (flats) when the shoot grew to the lid or when leaves were open. Transgenic plantlets were grown in flats until the 1st trifoliate leaf appeared and then transferred to 6 inch pots to grow to seed.

Example 7

Expressing a REV Transgene from an Embryo-Specific Promoter to Determine Increased Seed Size in Transgenic Soybean $T_0$ events harboring the LFAH12-AtREV gene-rev 3' UTR (TG GM6) transgene construct were selected for advancement for phenotype evaluation based on a combination of transgene expression and transgene insertion locus number. Events with verified transgene expression and a single transgene insertion locus were assigned the highest priority to be carried forward for seed expansion and field testing. In some instances, events with multiple insertion loci were selected if the presence of multiple genes gave a high overall transgene expression level due to gene dosage. $T_1$ seeds from selected $T_0$ events were grown as segregating $T_1$ populations in a greenhouse. Seeds were harvested from all $T_1$ plants individually. $T_2$ generation plants for each event were grown and typed by PCR to determine which $T_2$ lines were homozygous, heterozygous, or null segregants for the REV transgene. Seeds from each $T_2$ line were harvested, counted, and weighed. Based on the total seed weight and seed number for each $T_2$ line, a thousand seed weight (TSW) value was calculated for each line. The average TSW was then calculated for the homozygous, heterozygous, and null segregant classes of seeds for each event.

Two independent transformation events with REV expression driven by the LFAH12 embryo-specific promoter showed statistically significant increases in seed size for both homozygous and heterozygous lines relative to null segregant lines. The results summarized in Table 4 demonstrate that overexpression of a REV transgene during early embryo development.

TABLE 4

Use of an embryo-specific promoter to evaluate the capacity of REV transgene to increase seed size in soybean as indicated by 1000 seed weight in homozygous and heterozygous transgenic plants relative to their null segregant sibling lines.

| Event | Zygosity | Number of lines | Avg. 1000 Seed Weight (g) | Standard Error | Seed Size Increase (%) |
|---|---|---|---|---|---|
| 2A4 | Homozygous | 32 | 69.8 | 1.03 | 5.8 |
| 2A4 | Heterozygous | 79 | 70.6 | 0.58 | 7.0 |
| 2A4 | Null | 38 | 66.0 | 0.97 | NA |
| 2B2 | Homozygous | 3 | 83.6 | 5.90 | 14.1 |
| 2B2 | Heterozygous | 19 | 79.5 | 2.33 | 8.5 |
| 2B2 | Null | 14 | 73.2 | 2.29 | NA |

Example 8

Expressing a REV Transgene from an Embryo-Specific Promoter to Determine Increased Total Seed Yield in Transgenic Soybean To test the effect of REV transgene expression driven by an embryo-specific promoter on total seed yield, T₃ seeds from homozygous and null segregant sibling lines were pooled and planted in the field during the summer growing season. All seeds harvested from individual plots in the field were dried at low heat in an oven to uniform moisture content before measuring seed weights. One transgenic event with REV expression driven by the LFAH12 embryo-specific promoter showed both increased total seed yield of 22.7% and increased seed size of 8.0% relative to its null sibling (Table 5).

TABLE 5

Use of an embryo-specific promoter to evaluate the capacity of a REV transgene to increase both seed size and yield in soybean comparing homozygous transgenic plants to null segregant sibling plants.

| Event | Zygosity | Total Seed Weight/100 Plants (g) | Total Seed Increase (%) | Avg. 1000 Seed Weight (g) | Seed Size Increase (%) |
|---|---|---|---|---|---|
| 2B2 | Homozygous | 1552 | 22.7 | 90.0 | 8.0 |
| 2B2 | Null | 1265 | NA | 83.3 | NA |

The previous examples are provided to illustrate, but not to limit, the scope of the claimed inventions. Other variants of the inventions will be readily apparent to those of ordinary skill in the art and encompassed by the appended claims. All publications, patents, patent applications and other references cited herein and are also incorporated by reference herein in their entirety.

What is claimed is:

1. A method for increasing seed size in a plant comprising over expressing a REV gene, wherein the REV gene is an *Arabidopsis thaliana* REV gene, and wherein the REV gene is under the control of a promoter associated with an oleate 12-hydroxylase:desaturase gene, or a leafy cotyledon gene (LEC2).

2. The method according to claim 1, wherein the promoter is heterologous or homologous to the plant.

3. The method according to claim 1, wherein the oleate 12-hydroxylase:desaturase promoter is the oleate 12-hydroxylase:desaturase gene promoter from *Lesquerella fendleri* (LFAH12), and the leafy cotyledon gene promoter is from *Arabidopsis thaliana*.

4. The method according to claim 1, wherein the plant is a monocot or a dicot.

5. The method according to claim 4, wherein the plant is a member of the Brassicaceae (Cruciferae), Gramineae, Malvaceae, or Leguminosae-Papilionoideae families.

6. The method according to claim 5, wherein the plant is canola, corn, camelina, cotton, alfalfa, soybean, wheat, rice, or barley.

7. A method for increasing the number of seeds obtainable from a plant comprising over expressing a REV gene, wherein the REV gene is an *Arabidopsis thaliana* REV gene, and wherein the REV gene is under the control of a promoter associated with an oleate 12-hydroxylase:desaturase gene, or a leafy cotyledon gene (LEC2).

8. The method according to claim 7, wherein the promoter is heterologous or homologous to the plant.

9. The method according to claim 7, wherein the oleate 12-hydroxylase:desaturase promoter is the oleate 12-hydroxylase:desaturase gene promoter from *Lesquerella fendleri* (LFAH12), and the leafy cotyledon gene promoter is from *Arabidopsis thaliana*.

10. The method according to claim 7, wherein the plant is a monocot or a dicot.

11. The method according to claim 10, wherein the plant is a member of the Brassicaceae (Cruciferae), Gramineae, Malvaceae, or Leguminosae-Papilionoideae families.

12. The method according to claim 11, wherein the plant is canola, corn, camelina, cotton, alfalfa, soybean, wheat, rice, or barley.

13. A method for the production of a transgenic plant having increased seed size, the method comprising: (a) introducing into a plant or into a plant cell, a REV gene, wherein the REV gene is an *Arabidopsis thaliana* REV gene, and wherein the REV gene is under the control of a promoter associated with an oleate 12-hydroxylase:desaturase gene, or a leafy cotyledon gene (LEC2); and (b) cultivating the plant or plant cell comprising the REV gene under conditions promoting regeneration and mature plant growth.

14. The method according to claim 13, wherein the plant or plant cell is derived from a plant which is a monocot or a dicot.

15. The method according to claim 14, wherein the plant is a member of the Brassicaceae (Cruciferae), Gramineae, Malvaceae, or Leguminosae-Papilionoideae families.

16. The method according to claim 15, wherein the plant is canola, corn, camelina, cotton, alfalfa, soybean, wheat, rice, or barley.

17. A method for the production of a transgenic plant having increased seed number, the method comprising: (a) introducing into a plant or into a plant cell, a REV gene, wherein the REV gene is an *Arabidopsis thaliana* REV gene, and wherein the REV gene is under the control of a promoter associated with an oleate 12-hydroxylase:desaturase gene, or a leafy cotyledon gene (LEC2); and (b) cultivating the plant or plant cell comprising the REV gene under conditions promoting regeneration and mature plant growth.

18. The method according to claim 17, wherein the plant or plant cell is derived from a plant which is a mono cot or a dicot.

19. The method according to claim 18, wherein the plant is a member of the Brassicaceae (Cruciferae), Gramineae, Malvaceae, or Leguminosae-Papilionoideae families.

20. The method according to claim 19, wherein the plant is canola, corn, camelina, cotton, alfalfa, soybean, wheat, rice, or barley.

21. A method for the production of a transgenic plant having increased seed size and increased seed number, the method comprising: (a) introducing into a plant or into a plant cell, a REV gene, wherein the REV gene is an *Arabidopsis thaliana* REV gene, and wherein the REV gene is under the control of a promoter associated with an oleate 12-hydroxylase:desaturase gene, or a leafy cotyledon gene (LEC2); and (b) cultivating the plant or plant cell comprising the REV gene under conditions promoting regeneration and mature plant growth.

22. The method according to claim 21, wherein the plant or plant cell is derived from a plant which is a monocot or a dicot.

23. The method according to claim 22, wherein the plant is a member of the Brassicaceae (Cruciferae), Gramineae, Malvaceae, or Leguminosae-Papilionoideae families.

24. The method according to claim 23, wherein the plant is canola, corn, camelina, cotton, alfalfa, soybean, wheat, rice, or barley.

* * * * *

```
                         SEQUENCE LISTING

<160> NUMBER OF SEQ ID NOS: 23

<210> SEQ ID NO 1
<211> LENGTH: 2529
<212> TYPE: DNA
<213> ORGANISM: Arabidopsis thaliana

<400> SEQUENCE: 1
atggagatgg cggtggctaa ccaccgtgag agaagcagtg acagtatgaa tagacattta      60
gatagtagcg gtaagtacgt taggtacaca gctgagcaag tcgaggctct tgagcgtgtc     120
tacgctgagt gtcctaagcc tagctctctc cgtcgacaac aattgatccg tgaatgttcc     180
attttggcca atattgagcc taagcagatc aaagtctggt ttcagaaccg caggtgtcga     240
gataagcaga ggaaagaggc gtcgaggctc cagagcgtaa accggaagct ctctgcgatg     300
aataaactgt tgatggagga gaatgatagg ttgcagaagc aggtttctca gcttgtctgc     360
gaaaatggat atatgaaaca gcagctaact actgttgtta acgatccaag ctgtgaatct     420
gtggtcacaa ctcctcagca ttcgcttaga gatgcgaata gtcctgctgg attgctctca     480
atcgcagagg agactttggc agagttccta tccaaggcta caggaactgc tgttgattgg     540
gttcagatgc ctgggatgaa gcctggtccg gattcggttg gcatctttgc catttcgcaa     600
agatgcaatg gagtggcagc tcgagcctgt ggtcttgtta gcttagaacc tatgaagatt     660
gcagagatcc tcaaagatcg gccatcttgg ttccgtgact gtaggagcct tgaagttttc     720
actatgttcc cggctggtaa tggtggcaca atcgagcttg tttatatgca gacgtatgca     780
ccaacgactc tggctcctgc ccgcgatttc tggaccctga gatacacaac gagcctcgac     840
aatgggagtt ttgtggtttg tgagaggtcg ctatctggct ctggagctgg gcctaatgct     900
gcttcagctt ctcagtttgt gagagcagaa atgctttcta gtgggtattt aataaggcct     960
tgtgatggtg gtggttctat tattcacatt gtcgatcacc ttaatcttga ggcttggagt    1020
gttccggatg tgcttcgacc cctttatgag tcatccaaag tcgttgcaca aaaaatgacc    1080
atttccgcgt gcggtatat caggcaatta gcccaagagt ctaatggtga agtagtgtat    1140
ggattaggaa ggcagcctgc tgttcttaga acctttagcc aaagattaag cagggcttc    1200 aatgatgcgg ttaatgggtt tggtgacgac gggtggtcta cgatgcattg tgatggagcg    1260
gaagatatta tcgttgctat taactctaca aagcatttga ataatatttc taattctctt    1320
```

```
tcgttccttg gaggcgtgct ctgtgccaag gcttcaatgc ttctccaaaa tgttcctcct    1380
gcggttttga tccggttcct tagagagcat cgatctgagt gggctgattt caatgttgat    1440
gcatattccg ctgctacact taaagctggt agctttgctt atccgggaat gagaccaaca    1500
agattcactg ggagtcagat cataatgcca ctaggacata caattgaaca cgaagaaatg    1560
ctagaagttg ttagactgga aggtcattct cttgctcaag aagatgcatt tatgtcacgg    1620
gatgtccatc tccttcagat ttgtaccggg attgacgaga atgccgttgg agcttgttct    1680
gaactgatat ttgctccgat taatgagatg ttcccggatg atgctccact tgttccctct    1740
ggattccgag tcatacccgt tgatgctaaa acgggagatg tacaagatct gttaaccgct    1800
aatcaccgta cactagactt aacttctagc cttgaagtcg gtccatcacc tgagaatgct    1860
tctggaaact cttttctag ctcaagctcg agatgtattc tcactatcgc gtttcaattc    1920
ccttttgaaa acaacttgca agaaaatgtt gctggtatgg cttgtcagta tgtgaggagc    1980
gtgatctcat cagttcaacg tgttgcaatg gcgatctcac cgtctgggat aagcccgagt    2040
ctgggctcca aattgtcccc aggatctcct gaagctgtta ctcttgctca gtggatctct    2100
caaagttaca gtcatcactt aggctcggag ttgctgacga ttgattcact tggaagcgac    2160
gactcggtac taaaacttct atgggatcac caagatgcca tcctgtgttg ctcattaaag    2220
ccacagccag tgttcatgtt tgcgaaccaa gctggtctag acatgctaga gacaacactt    2280
gtagccttac aagatataac actcgaaaag atattcgatg aatcgggtcg taaggctatc    2340
tgttcggact tcgccaagct aatgcaacag ggatttgctt gcttgccttc aggaatctgt    2400
gtgtcaacga tgggaagaca tgtgagttat gaacaagctg ttgcttggaa agtgtttgct    2460
gcatctgaag aaaacaacaa caatctgcat tgtcttgcct tctcctttgt aaactggtct    2520
tttgtgtga                                                            2529
```

<210> SEQ ID NO 2
<211> LENGTH: 60
<212> TYPE: PRT
<213> ORGANISM: Arabidopsis thaliana

<400> SEQUENCE: 2

```
Asn Leu Val Tyr Glu Asn Gly Phe Met Lys His Arg Ile His Thr Ala
1               5                   10                  15

Ser Gly Thr Thr Thr Asp Asn Ser Cys Glu Ser Val Val Ser Gly
            20                  25                  30

Gln Gln Arg Gln Gln Gln Asn Pro Thr His Gln His Pro Gln Arg Asp
        35                  40                  45

Val Asn Asn Pro Ala Asn Leu Leu Ser Ile Ala Glu
    50                  55                  60
```

<210> SEQ ID NO 3
<211> LENGTH: 60
<212> TYPE: PRT
<213> ORGANISM: Arabidopsis thaliana

<400> SEQUENCE: 3

```
Asn Leu Val Tyr Glu Asn Gly His Met Lys His Gln Leu His Thr Ala
1               5                   10                  15

Ser Gly Thr Thr Thr Asp Asn Ser Cys Glu Ser Val Val Ser Gly
            20                  25                  30

Gln Gln His Gln Gln Gln Asn Pro Asn Pro Gln His Gln Gln Arg Asp
        35                  40                  45

Ala Asn Asn Pro Ala Gly Leu Leu Ser Ile Ala Glu
```

<210> SEQ ID NO 4
<211> LENGTH: 47
<212> TYPE: PRT
<213> ORGANISM: Arabidopsis thaliana

<400> SEQUENCE: 4

Gln Leu Val Cys Glu Asn Gly Tyr Met Lys Gln Gln Leu Thr Thr Val
1               5                   10                  15

Val Asn Asp Pro Ser Cys Glu Ser Val Val Thr Thr Pro Gln His Ser
            20                  25                  30

Leu Arg Asp Ala Asn Ser Pro Ala Gly Leu Leu Ser Ile Ala Glu
        35                  40                  45

<210> SEQ ID NO 5
<211> LENGTH: 50
<212> TYPE: PRT
<213> ORGANISM: Brassica napus

<400> SEQUENCE: 5

His Leu Val Ser Glu Asn Gly Tyr Met Gln Gln Gln Leu Thr Leu Thr
1               5                   10                  15

Thr Leu Gly Thr Asp Ala Ser Cys Asp Ser Val Asp Pro Thr Pro Pro
            20                  25                  30

Leu His Pro Leu Arg Asp Ala Asn Ser Pro Ala Gly Leu Met Ala Ile
        35                  40                  45

Ala Glu
    50

<210> SEQ ID NO 6
<211> LENGTH: 49
<212> TYPE: PRT
<213> ORGANISM: Oryza sativa

<400> SEQUENCE: 6

Gln Leu Val His Glu Asn Ala His Met Arg Gln Gln Leu Gln Asn Thr
1               5                   10                  15

Pro Leu Ala Asn Asp Thr Ser Cys Glu Ser Asn Val Thr Thr Pro Gln
            20                  25                  30

Asn Pro Leu Arg Asp Ala Ser Asn Pro Ser Gly Leu Leu Ser Ile Ala
        35                  40                  45

Glu

<210> SEQ ID NO 7
<211> LENGTH: 49
<212> TYPE: PRT
<213> ORGANISM: Zea mays

<400> SEQUENCE: 7

Gln Leu Val His Glu Asn Ala His Met Lys Gln Gln Leu Gln Asn Thr
1               5                   10                  15

Ser Leu Ala Asn Asp Thr Ser Cys Glu Ser Asn Val Thr Thr Pro Pro
            20                  25                  30

Asn Pro Leu Arg Asp Ala Ser Asn Pro Ser Gly Leu Leu Ala Ile Ala
        35                  40                  45

Glu

<210> SEQ ID NO 8
<211> LENGTH: 49

<212> TYPE: PRT
<213> ORGANISM: Oryza sativa

<400> SEQUENCE: 8

Gln Leu Val His Glu Asn Ala Tyr Met Lys Gln Gln Leu Gln Asn Pro
1               5                   10                  15

Ser Leu Gly Asn Asp Thr Ser Cys Glu Ser Asn Val Thr Thr Pro Gln
            20                  25                  30

Asn Pro Leu Arg Asp Ala Ser Asn Pro Ser Gly Leu Leu Thr Ile Ala
        35                  40                  45

Glu

<210> SEQ ID NO 9
<211> LENGTH: 55
<212> TYPE: PRT
<213> ORGANISM: Arabidopsis thaliana

<400> SEQUENCE: 9

Gln Leu Val His Glu Asn Ser Tyr Phe Arg Gln His Thr Pro Asn Pro
1               5                   10                  15

Ser Leu Pro Ala Lys Asp Thr Ser Cys Glu Ser Val Val Thr Ser Gly
            20                  25                  30

Gln His Gln Leu Ala Ser Gln Asn Pro Gln Arg Asp Ala Ser Pro Ala
        35                  40                  45

Gly Leu Leu Ser Ile Ala Glu
    50                  55

<210> SEQ ID NO 10
<211> LENGTH: 56
<212> TYPE: PRT
<213> ORGANISM: Arabidopsis thaliana

<400> SEQUENCE: 10

His Leu Val Tyr Glu Asn Ser Tyr Phe Arg Gln His Pro Gln Asn Gln
1               5                   10                  15

Gly Asn Leu Ala Thr Thr Asp Thr Ser Cys Glu Ser Val Val Thr Ser
            20                  25                  30

Gly Gln His His Leu Thr Pro Gln His Gln Pro Arg Asp Ala Ser Pro
        35                  40                  45

Ala Gly Leu Leu Ser Ile Ala Asp
    50                  55

<210> SEQ ID NO 11
<211> LENGTH: 809
<212> TYPE: DNA
<213> ORGANISM: Arabidopsis thaliana

<400> SEQUENCE: 11
ggttgcatct tgaatacct tttctcatt taggcataac aatataataa tttgtttttt      60
gttttcattt tcttttggtg tcatcttcaa aaatctgtaa acccaaaagt ttgtataact    120
tgtttattaa gatatttta attaaatttt ttttttgac attttaaaa aattataaag      180 tgttttatga atttaaggag taaataatat ttatttagaa cactataaat tagttttaca    240
agttcttaga aatgtatctg taaatttcaa aaaggaaaaa tatagcattt aatttttgaag  300 atttttttct acattatata tatgataaaa atattgtatt ttgtactttg tagttacaaa   360
aagtcattat atcaacaaat ctaaatataa aatatttttc tatatattac tccaaattaa   420
ctgtcagaat aaaaaagaag aataattatt acagaatctg aacattaaaa tcgtccctcc   480

-continued

| | |
|---|---|
| atatgtggtc tctgtctagt ccaaaagcaa tttacacatc ccaagccgaa actatattaa | 540 |
| ataaacattt ttttttcttt aactaaaaca tttataacat ttaacaataa aagttaaaaa | 600 |
| tcgaacacgt ataacgtatt tttttacgta tacgtcttgt tggcatatat gcttaaaaac | 660 |
| ttcattacat acatatacaa gtatgtctat atatatgata ttatgcaaac acaaatctgt | 720 |
| tgactataat tagacttctt catttactct ctctctgact taaaacattt attttatctt | 780 |
| cttcttgttc tctcttctc tttctctca | 809 |

<210> SEQ ID NO 12
<211> LENGTH: 2170
<212> TYPE: DNA
<213> ORGANISM: Lesquerella fendlesi

<400> SEQUENCE: 12

| | |
|---|---|
| tcaggaagat taagtctttg cttgttgtct gatttctttt aaatacatta agaaatcggt | 60 |
| tatgaagctt cgttttttgt gttttgggat tatgaagctg tctttggata ttagttgcgg | 120 |
| ttattagcat gcttctcttt tgtgttttgg ggatgatgaa gcagggtctc tctatgtaat | 180 |
| gcattttgtt tgaaaactca gctaatgcta atgcaatttc ttttgaaacc tttgttatgt | 240 |
| tttcaaaaat attgaatagg ttctgttatg gatttatttg caaaagccat tgattaaatc | 300 |
| aaaccattac ataagaacaa cattcattat taactaatta gagatgcaaa acacaacatt | 360 |
| acatacaaca tcagtgacta attattgaga caaaacaaca tcacagacac aaacattcat | 420 |
| ctcatacatc acttagagag acacaaaaag caaccaaaca caactattcc gccaacaaca | 480 |
| attagcttca tacgttttgc ttctcctttc aagccttcaa tcatcttctc acagccacga | 540 |
| atctgagcct tcaataataa catttcttca tcgtgacact tctcacggtt atgaatgcaa | 600 |
| gcctttatgt cctctacttc ttctactaaa gacacatcgg tccacttcca ggtgtggaat | 660 |
| cctcctcttt tgaaattttt ctcacaggta tggaataatc tacctgggtt ttttggagtt | 720 |
| cttgaggttc tgatcacaac acggcatcca catcgacagg tcttaggaaa accacgaagg | 780 |
| ttatgatctt caagctcact gtcaaaagat aaaaacgagt ttgaagaaga agaaggcatt | 840 |
| atcaatttca gagaattttg gagaattttg agagattgag aattgggaaa taagaacct | 900 |
| aatccccaat ttatgagatt gaaaatatat ccgttagaga agaaactaaa tgttgtgcgt | 960 |
| tttaattaga aaaaatagag atgggcttta tcttttgtta agagttttgg gcttgggctt | 1020 |
| gggtttttga taaaaaaatt aattaaacca aaacgacgtc gtttggttta attgttgtta | 1080 |
| aaaaaaaatt aaaacaccaa aacgacgtcg ttttggtgtt attaacgcc ttaaaacgga | 1140 |
| ttaaatccat aatccgtcag tcaactaggg ttacggatgg tcaacggcgt ttttgcataa | 1200 |
| cggaggcaca gttcaggctt aacggagtgg acggaatggc ttttaggaa gtttgtaacc | 1260 |
| ggggtctttt gtttatgatg tatttgtccc cgtcggctat tgttcaggcc gtttaggcct | 1320 |
| ttttcctata tactgaaaat aactattgtc cagacgagtt acttctccaa catatcaaga | 1380 |
| agtgttacaa agatgtgtta cgaagccata aaactcaaaa ccctaagcct aaaccctaga | 1440 |
| actttctagc acgtttatac cttctccttt ctttagtttc cttaaaggc cttcgtatca | 1500 |
| taagttttat ttttgcttaa tactaacact agaaaaaaac aataatcaac ataaactagg | 1560 |
| ttaagtcgtg gatctaattt tattgtgaaa atgtaattgc ttctcttaag aaaagattca | 1620 |
| tagcaaaata ttcgcatctt tcttgtgaat catcttttgt ttttggggct attaaagaaa | 1680 |
| aattgaactc atgaaatggt gacaacttta ttctagaggt aacagaacaa aaatatagga | 1740 |
| acaacacgtg ttgttcataa actacacgta taatactcaa gaagatgaat ctttataaga | 1800 |

```
atttagttttt ctcatgaaaa cataaaaagt tttgtcaatt gaaagtgaca gttgaagcaa    1860
aggaacaaaa ggatggttgg tgatgatgct gaaatgaaaa tgtgtcattc atcaaatact    1920
aaatactaca ttacttgtca ctgcctactt ctcctctttc ctccgccacc catttttggac   1980 ccacgagcct tccatttaaa ccctctctcg tgctattcac cagaatagaa gccaagagag    2040
agagagagat tgtgctgagg atcattgtct tcttcatcgt tattaacgta agttttttt     2100 tgaccactta tatctaaaat ctagtacatg caatagatta atgactgttc cttcttttga    2160
tattttcagc                                                           2170

<210> SEQ ID NO 13
<211> LENGTH: 1255
<212> TYPE: DNA
<213> ORGANISM: Arabidopsis thaliana

<400> SEQUENCE: 13
ctttgttttg tagagtgttc tatgggttat gatttcgaaa agaaaaaaaa ttgtgagaca      60
cttaataaaa ttatttcgac aaaaaaagta gcttgtataa aaaaatcaga ttttaattta    120
tgtaagaaca aattccaata tccaatagtt aaaaataatt atttgttccg attaatcgag    180
ttttgcaaaa tatgcacaaa atctatcatg taccatttct aagactatat atttggttat    240
atattttatg ccgtgtgttc tgattccaat aaatttttagc gcatagtaaa ttttctaaaa   300
agcaaaattt tctcaaaagt gtactaatga caattaattg agtttctaca aaataagaat    360
aactattgac tcgattttca caaaactagt atgctaaata tcacattact tttaaaatta    420
aatggaatta tcttttttcaa tattggatac gaataatttt tacactaaag ttatttttaat  480 aaaataaccg tttattcaaa atatgtaaag acgacaaaaa tatatattaa atggaaaaac    540
gactaactta gttttttgcaa aattaaatgg atttgtccctt ttcaatgttt gaatacaaaa  600
aaaaatctat aataagttta ttatattaaa ataacccgtt ttttcagaat acgcaaaaac    660
gacaaaaaaa tattaattac aaagaaattt agtttataca aaaatatgaa tggctattaa    720
tggtgtttac tctaaattta attattatgc atttatgcta atctttctaa aaggtacaaa    780 gattcgttttt ttcaatgttt gaactgcata ttaaggtata gatttggacc ttaacagagt   840
taatatataa ggaagagagc caaggaactc caaaataaaa taaagagcct tctctctctc    900
tctctgagaa aaaacacata tagccaatga ccttctcgtg gtcttctgtg ccataaaagc    960
cattatatac attcaaacac aatctggcgc cacatataca catgtactag tgtatgtata   1020
tgtcctaacc tctgtattca tatctctctc cttgtctgag tggtgcgatg ggtatcccca   1080
taagctgcaa acattgaacc atctgcaaca ttttgactcg ttttcttttg tgtttttcca   1140
acatctgtct cttcttcact cgctctctcc taatcaatct ccccaacgac ctctcttttt   1200
ttttgtttct tcactcagat ctctctccct ctctctctct ctctctccgg gaaaa        1255

<210> SEQ ID NO 14
<211> LENGTH: 30
<212> TYPE: DNA
<213> ORGANISM: Artificial
<220> FEATURE:
<223> OTHER INFORMATION: Oligonucleotide primer

<400> SEQUENCE: 14
gaattctcag gaagattaag tctttgcttg                                      30

<210> SEQ ID NO 15
<211> LENGTH: 31
<212> TYPE: DNA
```

-continued

<213> ORGANISM: Artificial
<220> FEATURE:
<223> OTHER INFORMATION: Oligonucleotide primer

<400> SEQUENCE: 15
gagctcgctg aaaatatcaa agaaggaac a                              31

<210> SEQ ID NO 16
<211> LENGTH: 30
<212> TYPE: DNA
<213> ORGANISM: Artificial
<220> FEATURE:
<223> OTHER INFORMATION: Oligonucleotide primer

<400> SEQUENCE: 16
gaattcggtt gcatctttga ataccttttt                               30

<210> SEQ ID NO 17
<211> LENGTH: 31
<212> TYPE: DNA
<213> ORGANISM: Artificial
<220> FEATURE:
<223> OTHER INFORMATION: Oligonucleotide primer

<400> SEQUENCE: 17
gagctctgag agaaagagaa agagagaaca a                             31

<210> SEQ ID NO 18
<211> LENGTH: 23
<212> TYPE: DNA
<213> ORGANISM: Artificial
<220> FEATURE:
<223> OTHER INFORMATION: Oligonucleotide primer

<400> SEQUENCE: 18
ccatggagat ggcggtggct aac                                      23

<210> SEQ ID NO 19
<211> LENGTH: 33
<212> TYPE: DNA
<213> ORGANISM: Artificial
<220> FEATURE:
<223> OTHER INFORMATION: Oligonucleotide primer

<400> SEQUENCE: 19
ggatcctcac acaaaagacc agtttacaaa gga                           33

<210> SEQ ID NO 20
<211> LENGTH: 24
<212> TYPE: DNA
<213> ORGANISM: Artificial
<220> FEATURE:
<223> OTHER INFORMATION: Oligonucleotide primer

<400> SEQUENCE: 20
gatatcttcg attgacagaa aaag                                     24

<210> SEQ ID NO 21
<211> LENGTH: 36
<212> TYPE: DNA
<213> ORGANISM: Artificial
<220> FEATURE:
<223> OTHER INFORMATION: Oligonucleotide primer

<400> SEQUENCE: 21
gcggccgcgg taccctcaac caaccacatg gaacca                        36

```
<210> SEQ ID NO 22
<211> LENGTH: 26
<212> TYPE: DNA
<213> ORGANISM: Artificial
<220> FEATURE:
<223> OTHER INFORMATION: Oligonucleotide primer

<400> SEQUENCE: 22
gcggccgctt cgattgacag aaaaag                                          26

<210> SEQ ID NO 23
<211> LENGTH: 36
<212> TYPE: DNA
<213> ORGANISM: Artificial
<220> FEATURE:
<223> OTHER INFORMATION: Oligonucleotide primer

<400> SEQUENCE: 23
gcggccgcgg taccctcaac caaccacatg gaacca                               36
```